(12) United States Patent
Boyer et al.

(10) Patent No.: US 12,285,521 B2
(45) Date of Patent: *Apr. 29, 2025

(54) PHARMACEUTICAL FORMULATION

(71) Applicant: Klaria Pharma Holding AB, Uppsala (SE)

(72) Inventors: Scott Boyer, Uppsala (SE); Fredrik Hübinette, Uppsala (SE); Leif Ingemarsson, Uppsala (SE); Susan Suchdev, Uppsala (SE)

(73) Assignee: Klaria Pharma Holding AB, Uppsala (SE)

( * ) Notice: Subject to any disclaimer, the term of this patent is extended or adjusted under 35 U.S.C. 154(b) by 162 days.

This patent is subject to a terminal disclaimer.

(21) Appl. No.: 17/811,970

(22) Filed: Jul. 12, 2022

(65) Prior Publication Data

US 2023/0018732 A1     Jan. 19, 2023

Related U.S. Application Data

(63) Continuation of application No. 17/215,963, filed on Mar. 29, 2021, now abandoned, which is a continuation of application No. 16/349,840, filed as application No. PCT/EP2017/079217 on Nov. 14, 2017, now Pat. No. 11,007,144.

(30) Foreign Application Priority Data

Nov. 15, 2016  (GB) .................................. 1619324

(51) Int. Cl.
| | |
|---|---|
| *A61K 9/00* | (2006.01) |
| *A61K 31/4045* | (2006.01) |
| *A61K 31/734* | (2006.01) |
| *A61K 47/02* | (2006.01) |
| *A61K 47/10* | (2017.01) |

(52) U.S. Cl.
CPC .......... *A61K 9/006* (2013.01); *A61K 31/4045* (2013.01); *A61K 31/734* (2013.01); *A61K 47/02* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 5,288,497 | A | 2/1994 | Stanley et al. |
| 5,288,498 | A | 2/1994 | Stanley et al. |
| 5,785,989 | A | 7/1998 | Stanley et al. |
| 8,759,282 | B2 | 6/2014 | Stenberg et al. |
| 9,192,570 | B2 | 11/2015 | Wyse et al. |
| 9,833,461 | B2 | 12/2017 | Modi |
| 10,039,710 | B2 | 8/2018 | Potta et al. |
| 11,007,144 | B2 | 5/2021 | Boyer et al. |
| 11,219,600 | B2 | 1/2022 | Boyer et al. |
| 11,904,049 | B2 | 2/2024 | Boyer et al. |
| 12,005,140 | B2 | 6/2024 | Boyer et al. |
| 2004/0247649 | A1 | 12/2004 | Pearce et al. |
| 2005/0031675 | A1 | 2/2005 | Spence Leung et al. |
| 2006/0039959 | A1 | 2/2006 | Wessling |
| 2006/0110331 | A1 | 5/2006 | Dang et al. |
| 2008/0269347 | A1 | 10/2008 | Bruss et al. |
| 2009/0186107 | A1 | 7/2009 | Haber et al. |
| 2009/0221489 | A1 | 9/2009 | Stenberg et al. |
| 2009/0246273 | A1 | 10/2009 | Al-Ghananeem |
| 2010/0112050 | A1 | 5/2010 | Ryoo et al. |
| 2011/0033542 | A1 | 2/2011 | Myers et al. |
| 2014/0004045 | A1 | 1/2014 | Mendenhall et al. |
| 2014/0005218 | A1 | 1/2014 | Myers et al. |
| 2014/0178473 | A1 | 6/2014 | Lim et al. |
| 2014/0256823 | A1 | 9/2014 | McCarty |
| 2014/0271788 | A1 | 9/2014 | Myers et al. |
| 2015/0005356 | A1 | 1/2015 | Fleming |
| 2015/0096572 | A1 | 4/2015 | Hubinette |
| 2015/0224070 | A1 | 8/2015 | Boudy et al. |
| 2015/0297653 | A1 | 10/2015 | Speier |
| 2016/0051510 | A1 | 2/2016 | Allen et al. |
| 2016/0206627 | A1 | 7/2016 | Gosselin et al. |
| 2017/0049789 | A1 | 2/2017 | Bhalani et al. |
| 2017/0348251 | A1 | 2/2017 | Schobel et al. |
| 2017/0079907 | A1 | 3/2017 | Potta et al. |
| 2017/0165315 | A1 | 6/2017 | Karavas et al. |
| 2017/0290776 | A1 | 10/2017 | Schobel et al. |

(Continued)

FOREIGN PATENT DOCUMENTS

| | | |
|---|---|---|
| CA | 2487882 A1 | 12/2003 |
| CA | 3033570 A1 | 2/2017 |

(Continued)

OTHER PUBLICATIONS

Chen, Ming J. et al. (2006). "Film-Forming Polymers in Fast-Dissolve Oral Films", Annual Meeting and Exposition of the American Association of Pharmaceutical Scientists, Oct. 29-Nov. 2, 2006, San Antonio, TX, USA.

USPTO Notice of Allowance for U.S. Appl. No. 17/457,460, filed Dec. 3, 2021, titled "Pharmaceutical Formulation", dated Oct. 25, 2023.

Murata, Y., et al., Preparation of Fast Dissolving Films for Oral Dosage from Natural Polysaccharides, Materials, Mar. 2010, 4291-4299.

International Preliminary Report on Patentability for International Application No. PCT/EP2018/065223, "Pharmaceutical Formulation", dated Dec. 10, 2019.

"More Solutions to Sticky Problems", Brookfield AMETEK, accessed at https: //www.brookfieldengineeri ng. com/ - / media/ ametekbrookfield / tech%20sheets/more%20solutions%202017. pdf? la=en, 2017, 31 pages.

(Continued)

*Primary Examiner* — Nannette Holloman
(74) *Attorney, Agent, or Firm* — Hamilton, Brook, Smith & Reynolds, P.C.

(57) ABSTRACT

A film comprising an alginate salt of a monovalent cation or a mixture of alginate salts containing at least one alginate salt of a monovalent cation, and a triptan or a pharmaceutically acceptable salt thereof, are described. Methods for manufacturing such a film, and the use of such a film in the treatment of disease in a human patient, in particular migraine with or without aura, cluster headache, or trigeminal neuralgia, are also described.

20 Claims, 4 Drawing Sheets

(56) References Cited

U.S. PATENT DOCUMENTS

| | | |
|---|---|---|
| 2017/0290870 A1 | 10/2017 | Schaneville |
| 2018/0104195 A1 | 4/2018 | Schobel et al. |
| 2018/0117019 A1 | 5/2018 | Wang et al. |
| 2018/0125977 A1 | 5/2018 | Schobel et al. |
| 2020/0054550 A1 | 2/2020 | Boyer et al. |
| 2020/0246253 A1 | 8/2020 | Boyer et al. |
| 2021/0283047 A1 | 9/2021 | Boyer et al. |
| 2021/0346277 A1 | 11/2021 | Boyer et al. |
| 2021/0369601 A1 | 12/2021 | Boyer et al. |
| 2022/0160618 A1 | 5/2022 | Boyer et al. |
| 2022/0273584 A1 | 9/2022 | Boyer et al. |
| 2022/0280453 A1 | 9/2022 | Boyer et al. |
| 2024/0041761 A1 | 2/2024 | Boyer et al. |
| 2024/0165022 A1 | 5/2024 | Boyer et al. |

FOREIGN PATENT DOCUMENTS

| | | |
|---|---|---|
| CN | 101081218 | 12/2007 |
| CN | 101574330 | 11/2009 |
| CN | 102871984 | 1/2013 |
| CN | 102961365 | 3/2013 |
| CN | 105878171 A | 8/2016 |
| EP | 1897543 A1 | 3/2008 |
| EP | 2431028 A2 | 3/2012 |
| EP | 1976562 B1 | 2/2018 |
| GB | 933462 | 8/1963 |
| IN | 351KOL2006 | 4/2006 |
| KR | 20080023873 | 3/2008 |
| KR | 20140110778 | 9/2014 |
| RU | 2625836 C2 | 7/2017 |
| WO | WO 91/03236 A1 | 3/1991 |
| WO | WO 98/01134 A1 | 1/1998 |
| WO | WO 98/02182 A1 | 1/1998 |
| WO | WO 01/87276 A1 | 11/2001 |
| WO | WO 2003/101357 A1 | 5/2003 |
| WO | WO 2004/012720 A1 | 2/2004 |
| WO | WO 2004/045305 A1 | 6/2004 |
| WO | WO 2004/075877 A1 | 9/2004 |
| WO | WO 2005/004989 A2 | 1/2005 |
| WO | WO 2005/018323 A1 | 3/2005 |
| WO | WO 2005/048980 A1 | 6/2005 |
| WO | WO 2006/023976 A2 | 3/2006 |
| WO | WO 2006/095267 | 9/2006 |
| WO | WO 2006/096913 A1 | 9/2006 |
| WO | WO 2007/028247 A1 | 3/2007 |
| WO | WO 2007/049102 A1 | 5/2007 |
| WO | WO 2007/073346 A1 | 6/2007 |
| WO | WO 2007/125533 A2 | 11/2007 |
| WO | WO 2007/143674 A2 | 12/2007 |
| WO | WO 2008/034881 A1 | 3/2008 |
| WO | WO 2008/073918 A1 | 6/2008 |
| WO | WO 2008/095144 A2 | 8/2008 |
| WO | WO 2008/098195 A2 | 8/2008 |
| WO | WO 2009/126132 A1 | 10/2009 |
| WO | WO 2010/029374 A1 | 3/2010 |
| WO | WO 2011036521 | 3/2011 |
| WO | WO 2011/053251 A1 | 5/2011 |
| WO | WO 2012/117257 A1 | 9/2012 |
| WO | WO 2012/121461 A1 | 9/2012 |
| WO | WO 2013/015545 A1 | 1/2013 |
| WO | WO 2013/019187 A1 | 2/2013 |
| WO | WO 2013/052770 A1 | 4/2013 |
| WO | WO 2013/059629 A1 | 4/2013 |
| WO | WO 2013/171146 A1 | 11/2013 |
| WO | WO 2014/160404 A1 | 4/2014 |
| WO | 2014/144241 A1 | 9/2014 |
| WO | WO 2014/202088 A1 | 12/2014 |
| WO | WO 2015/025324 A1 | 2/2015 |
| WO | WO 2015/074663 A1 | 5/2015 |
| WO | WO 2015/160941 A1 | 10/2015 |
| WO | WO 2015/195708 A1 | 12/2015 |
| WO | WO 2016/024008 A1 | 2/2016 |
| WO | WO 2016/201286 A1 | 12/2016 |
| WO | WO 2017/003935 | 1/2017 |
| WO | WO 2017/020125 A1 | 2/2017 |
| WO | WO 2017/120492 A1 | 7/2017 |
| WO | WO 2017/132410 A1 | 8/2017 |
| WO | WO 2017/135195 A1 | 8/2017 |
| WO | WO 2017/180707 A1 | 10/2017 |
| WO | 2017218918 A1 | 12/2017 |
| WO | WO 2018/091473 A1 | 5/2018 |
| WO | WO 2018/224674 A1 | 12/2018 |
| WO | WO 2019/219773 A1 | 11/2019 |
| WO | WO 2019/224323 A1 | 11/2019 |
| WO | WO 2021028578 A1 | 2/2021 |
| WO | WO 2021/037960 A1 | 3/2021 |
| WO | 2021090309 A1 | 5/2021 |

OTHER PUBLICATIONS

Abd El Azim, H., et al., "Liposomal buccal mucuadhesive film for improved delivery and permeation of water-soluble vitamins", International Journal of Pharmaceutics, 2015, 488(1): 78-85.

Abdelkader et al., "Novel in situ gelling ocular films for the opioid growth factor-receptor antagonist-naltrexone hydrochloride: Fabrication, mechanical properties, mucoadhesion, tolerability and stability studies", Int J Pharmaceutics, 2014, 477(1-2), 631-642.

Alzheimer's Association: 10 Early Signs and Symptoms of Alzheimer's, 2018, accessed at https://www.alz.org/10-signs-symptoms-alzheimers-dementia.asp.

Asthana et al., "Formulation and Evaluation of Alginate-Based Mucoadhesive Buccal Patch for Delivery of Antimigraine Drug", Asian J Pharm Clin Res, 2018, 11(4), 185-191.

Bachelor et al. "Organotypic human oral tissue models for evaluation of oral care products", presented at Society of Toxicology 2014 annual meeting, Jan. 3-7, 2014; only abstract available via https://www.mattek.com/referencelibrary/organotypic-human-oral-tissue-models-for-evaluation-of-oral-careproducts/.

Bachynsky et al., "Factors Affecting the Efficiency of a Self-Emulsifying Oral Delivery System", Drug Dev Ind Pharm, 1997, 23, 809-816.

Basu et al., "Cannabinoid Receiptor 2 is Critical for the Homing and Retention of Marginal Zone B Lineage Cells and for Efficient T-Independent Immune Responses", J Immunol, 2011, 187(11), 5720-5732.

Begg et al., "Evidence for novel cannabinoid receptors", Pharmacology Et Therapuetics, 2005, 106(2), 133-145.

Ben Amar, M., "Cannabinoids in medicine: A review of their therapeutic potential", J Ethnopharmacol, 2006, 105(1-2), 1-25.

Bhagwati et al., "Bioavailability Enhancement of Rizatriptan Benzoate by Oral Disintegrating Strip: In Vitro and In vivo Evaluation", Current Drug Delivery, 2016, 13(3), 462-470.

Bouhassira et al., "Prevalence of chronic pain with neuropathic characteristics in the general population", Pain, 2008, 136(3), 380-387.

Bourassa et al., "Label-Free Monitoring of μ-Opioid Receptor-Mediated Signaling", Mot Pharmacol, 2014, 86(2), 138-149.

Chey, "Irritable Bowel Syndrome A Clinical Review", JAMA, 2015, 313(9), 949-958.

Date et al., "Self-nanoemulsifying drug delivery systems" formulation insights, applications and advances, Nanomedicine, 2010, 5(10), 1595-1616.

Davis and Brewster, "Cyclodextrin-Based Pharmaceutics: Past, Present and Future", Nat Rev Drug Discovery, Mar. 2004, 1023-1035.

Davis and Dickey, "Regulated Airway Goblet Cell Mucin Secretion", Annu Rev Physiol, 2008, 70, 487-512.

Dawson et al., "The In Vitro Cell Association of Invasin Coated Polylactide-Co-Glycolide Nanoparticles", Pharm Res, 2000, 17(11), 1420-1425.

Dechant et al., "Sumatriptan A Review of its Pharmacodynamic and Pharmacokinetic Properties, and Therapeutic Efficacy in the Acute Treatment of Migraine and Cluster Headache", Drugs, 1992, 43(5), 776-798.

Derry et al., "Sumatriptan (all routes of administration) for acute migraine attacks in adults—overview of Cochrane reviews (Review)", Cochrane Database of Systematic Reviews, May 2014, CD009108.

(56) References Cited

OTHER PUBLICATIONS

Dowling et al., "Population Phamacokinetics of Intravenous, Intramuscular, and Intranasal Naloxone in Human Volunteers", *Ther Drug Monit*, 2008, 30(4), 490-496.

Dusquesnoy et al.,"Comparative clinical pharmacokinetics of single doses of sumatriptan following subcutaneous, oral, rectal and intranasal administration", *Eur J Pharm Sci*, 1998, 6(2), 99-104.

ElSohly and Slade, "Chemical constituents of marijuana: The complex mixture of natural cannabinoids" *Life Sciences*, 2005, 78, 539-548.

European Pharmacopoeia, Feb. 2013, 1490-1492.

Ferrari et al., "Interindividual variability of oral sumatriptan pharmacokinetics and of clinical response in migraine patients", *Eur J Clin Pharmacol*, 2008, 64, 489-495.

FMC Biopolymer, Product Specification Bulletin for Protanal® LFR 5/60, version 3, Oct. 12, 2013.

FMC Biopolymer, Product Specification for Manucol® LB, 2013.

Fowler et al., "The Clinical Pharmacology, Pharmacokinetics and Metabolism of Sumatriptan", *Eur Neural*, 1991, 31, 291-294.

Friedl et al.,"Development and Evaluation of a Novel Mucus Diffusion Test System Approved by Self-Nanoemulsifying Drug Delivery systems", *Pharmaceutics, drug delivery and pharmaceutical technology*, 2013, 102, 4406-4413.

Gizurason et al., "Anatomical and Histological Factors Affecting Intranasal Drug and Vaccine Delivery", *Current Drug Delivery*, Sep. 2012, 566-582.

Grubstein and Milano, "Stabilization of epinephrine in a local anesthetic injectable solution using reduced levels of sodium metabisulfite and edta", *Drug Development and Industrial Pharmacy*, 1992, 18(14), 1549-1566.

Gupta et al.,"Design and Development of Oral Transmucosal Film for Delivery of Salbutamol Sulphate", *Journal of Pharmaceutical, Chemical and Biological Sciences*, 2014, 2(2), 118-129.

Haas and Harper, "Ketamine: A Review of Its Pharmacologic Properties and Use in Ambulatory Anesthesia", *Anesth Prag*, 1992, 39, 61-68.

He et al., "Adapting liposomes for oral drug delivery", *Acta Pharmaceutica Sinica B*, 2019, 36-48.

https://pubchem.ncbi.nlm.nih.gov/compound/naloxone, C19H21NO497 pages, downloaded on Aug. 13, 2019.

Hussain et al, "Utilizing Bacterial Mechanisms of Epithelial Cell Entry: Invasin-induced Oral Uptake of Latex Nanoparticles", Pharm Res, 1998, 15(1), 153-156.

International Preliminary Report on Patentability for International Application No. PCT/EP2017/079217, "Pharmaceutical Formulation", dated May 21, 2019.

International Search Report for International Application No. PCT/EP2017/079217, "Pharmaceutical Formulation", dated Jan. 30, 2019.

International Search Report for International Application No. PCT/EP2018/065223, "Pharmaceutical Formulation", dated Aug. 10, 2018.

Kaminski, "Inhibition of the CAMP signaling cascade via cannabinoid receptors: a putative mechanism of immune modulation by cannabinoid compounds", *Toxicology Lett*, 1998, 102-103, 59-63.

Klaria press releases dated Oct. 29, 2015, Feb. 24, 2016, Apr. 19, 2016, May 11, 2016, Jul. 1, 2016 and Aug. 15, 2016.

Lee and Mooney, "Alginate: properties and biomedical applications", *Prag Polym Sci*, 2012, 37(1 ), 106-126.

Lim, K., et al., "a Systematic Review of the Effectiveness of Medical Cannabis for Psychiatric, Movement and Neurodegenertive Disorders", Clinical Psychopharmacology and Neuroscience 2017; 15(4): 301-312.

Imigran Tablets, Injection and Nasal Spray. SmPC, 2007, 24.

Maas et al., "A model-based approach to treatment comparison in acute migraine", *Br J Clin Pharm*, 2007, 62(5), 591-600.

Managaro and Wertz, "The Effects of Permeabilizers on the In Vitro Penetration of Propranolol Through Porcine Buccal Epithelium", *Mil Med*, 1996, 161 (11 ), 669-672.

Marasini et al., "Development and Optimization of Self-Nanoemulsifying Drug Delivery system with Enhanced Bioavailability by Box-Behnken Design and Desirability Function", *J Pharm Sci*, 2012, 101, 4584-4596.

Market Size and Demand for Marijuana in Colorado http://www.cannabisconsumer.org/uploads/9/7 /9/6/97962014/market size and demand studyJuly 9 2014%5B1%5D.pdf.

Marttin et al., "The effect of methylated β-cyclodextrins on the tight junctions of the rat nasal respiratory epithelium: Electron Microscopic and confocal laser scanning microscopic visualization studies", *J Control Release*, 1999, 57, 205-213.

McLean-Tooke et al., "Adrenaline in the treatment of anaphylaxis: what is the evidence?" *BMJ*, 2003, 327(7427), 1332-1335.

Mechoulam et al., "Cannabidiol—Recent Advances" *Chemistry Et Biodiversity*, Apr. 2007, 1678-1692.

Merkus et al., "Cyclodestrins in nasal drug delivery", *Adv Drug Del Rev*, 1999, 36, 41-57.

Muller et al., "Ketamine enantiomers in the rapid and sustained antidepressant effects", *Ther Adv Psychopharmacol*, Jun. 2016, 185-192.

Nadel, "Acute effects of inhalation of cigarette smoke on airway conductance", *J Appl Physiol*, 1961, 16, 713-716.

Nicholson, Ulcerative Colitis Statistics, 2016, accessed at InflammatoryBowelDisease.net, Sep. 30, 2019, 2 pages.

Niddk, Definition and Facts for Crohn's Disease, 2017, accessed at https: / /www. niddk. nih. gov/health-information/ digestive-diseases/ crohnsdisease/definition-facts.

Non-Final Office Action for U.S. Appl. No. 16/349,840 "Pharmaceutical Formulation" dated Oct. 6, 2020.

Notice of Allowance for U.S. Appl. No. 16/349,840 "Pharmaceutical Formulation" dated Jan. 14, 2021.

Oesterling, "The adverse effect of ascorbic acid on the stability of adrenaline and noadrenaline solutions", *Biochim Biophys Acta*, 1957, 24(1), 178-187.

Office Action for U.S. Appl. No. 16/607,892, "Pharmaceutical Formulation" dated Feb. 25, 2021.

Owen et al., "The Preclinical toxicological evaluation of sumatriptan", *Human Et Experimental Toxicology*, 1995, 14, 959-973.

Ozaki et al., "Inhibition of Crystal Nucleation and Growth by Water-Soluble Polymers and its Impact on the Supersaturation Profiles of Amorphous Drugs", *J Pharm Sci*, 2013, 102, 2273-2281.

Parish et al.,"A systematic review of epinephrine degradation with exposure to excessive heat or cold", *Annals of Allergy, Asthma Et Immunology*, 2016, 117(1), 79-87.

Paudel et al., "Cannabidiol bioavailability after nasal and transdermal application: effect of permeation enhancers", *Drug Dev Ind Pharm*, 2010, 36, 1088-1097.

Pertwee, "The pharmacology of cannabinoid receptors and their ligands: an overview", *IntJObesity*, 2006, 30, S13-S18.

Pouton, "Formulation of poorly water-soluble drugs for oral administration: Physicochemical and physiological issues and the lipid formulation classification system", *European Journal of Pharmaceutical Sciences*, 2006, 29(3-4), 278-287.

Prachayasittikul et al., "EDTA-induced Membrane Fluidization and Destabilization: Biophysical Studies on Artificial Lipid Membranes", *Acta biochimica et biophysica Sinica*, 2007, 39(11 ), 901-913.

Pradhan et al., "Fabrication of a uniformly sized fenofibrate microemulsion by membrane emulsification", *J Microencapsul*, 2013, 30, 42-48.

Sayed et al., "Fast-Dissolving Sublingual Films of Terbutaline Sulfate: Formulation and In Vitro/In Vivo Evaluation", *Mot Pharmaceutics*, 2013, 10(8), 2942-2947.

Shannon, R.D. "Revised Effective Ionic Radii and Systematic Studies of Interatomic in Halides and Chalcogenides", Act Cryst. (1976) A 22, 751.

Sharma et al., "Development and Characterization of Self Emulsifying Drug Delivery system of a Poorly Water Soluble Drug Using Natural Oil", *Acta Pol Pharm*, 2012, 69, 713-717.

Shojaei, "Buccal Mucosa As a Route for Systemic Drug Delivery: A Review", *J Pharmaceut Sci*, 1998, 1 (1) 15-30.

(56) References Cited

OTHER PUBLICATIONS

Shtenberg et al., "Mucoadhesive alginate pastes with embedded liposomes for local oral drug delivery", Int J Biol Macromol, 2018, 111, 62-69.
Simons, "Epinephrine absorption in children with a history of anaphylaxis", *J Clin Immunol*, 1998, 101, 33-37.
Sinner and Graf, "Ketamine" in *Modern Anesthetics: Handbook of Experimental Pharmacoogy*. Eds. Schuttler and Schwilden, 182, 313-333 (2008).
Skulason et al., "Evaluation of polymeric films for buccal drug delivery", *Pharmazie*, 2009, 64(3), 197-201.
Sperger et al., "Analysis of Composition, Molecular Weight, and Water Content Variations in Sodium Alginate Using Solid-State NMR Spectroscopy", *J Pharmaceut Sci*, 2011, 100, 3441-3452.
Squier and Wertz. "Structure and function of the oral mucosa and implications for drug delivery" in *Oral mucosa[ drug delivery*. Ed. Rathbone; pub. Dekker, Jan. 25, 1996.
Stepensky et al., "Long-Term Stability Study of $\lfloor$-Adrenaline Injections: Kinetics of Sulfonatation and Racemization Pathways of Drug Degradation", *J Pharmaceut Sci*, 2004, 93(4), 969-980.
Stout and Cimino, "Analysis of Composition, Molecular Weight, and Water Content Variations in Sodium Alginate Using Solid-State NMR Spectroscopy", *Drug Met Rev*, 2014, 46(1), 86-95.
Tashkin, "Acute Effects of Smoked Marijuana and Oral $\Delta^\circ$-Tetrahydrocannabinol on Specific Airway Conductance in Asthmatic Subjects[1-3]", *Am Rev Respir Dis*, 1974, 109, 420-428.
Tayel et al., "Sumatriptan succinate sublingual fast dissolving thin films: formulation and in vitro/invivo evaluation", *Pharm Dev Technol*, 2016, 31, 328-337.
Thakur et al., "Transdermal and Buccal Delivery of Methylxanthines Through Human Tissue in Vitro",*Drug Dev. Ind. Pharm.*, 2007, 33(5), 513-521.
Tuleu et al., "Short term stability of pH-adjusted lidocaine-adrenaline epidural solution used for emergency caesarean section", *International Journal of Obstetric Anesthesia*, 2008, 17(2), 118-122.
Tylleskar et al., "Pharmacokinetics of a new, nasal formulation of naloxone", *Eur J Clin Pharmacol*, 2017, 73, 555-562.
Written Opinion for International Application No. PCT/EP2017/079217, "Pharmaceutical Formulation", dated May 21, 2019.
Written Opinion for International Application No. PCT/EP2018/065223, "Pharmaceutical Formulation", dated Aug. 10, 2018.
www.drugs.com/imitrex html, downloaded Aug. 13, 2019, 6 pages.
www.drugs.com/monograph/sumatriptan.html, downloaded Aug. 13, 2019, 28 pages.
www.drugs.com/naloxone.html, downloaded on Mar. 29, 2021.
www.epipen.com/hcp/media/files/epipen/prescribing_information.pdf, Aug. 2012, 2 pages.
www.mannamolecular.com/2016/09/forms-of-cannabis-intake, downloaded Aug. 13, 2019, 6 pages.
www.migraine.com/migraine-treatment/nasal-spray, downloaded Aug. 13, 2019, 6 pages.
www.niddk.nih.gov/health-information/digestive-diseases/chrons-disease, downloaded Aug. 13, 2019, 3 pages.
Zgair et al., "Development of a simple and sensitive HPLC-UV method for the simultaneous determination of cannabidiol and $\Delta^9$-tetrahydrocannabinol in rat plasma" *J Pharmaceut Biomed Anal*, 2015, 114, 145-151.
Written Opinion of the International Searching Authority for International Application No. PCT/EP2019/063376, "Pharmaceutical Formulation" Dated Jul. 29, 2019.
International Search Report for International Application No. PCT/EP2019/063376, "Pharmaceutical Formulation" Dated Jul. 29, 2019.
International Preliminary Report on Patentability for International Application No. PCT/EP2019/063376, "Pharmaceutical Formulation" Dated Jul. 29, 2019.
Written Opinion of the International Searching Authority for International Application No. PCT/EP2019/062534, "Pharmaceutical Formulation" Dated Jul. 29, 2019.
International Search Report for International Application No. PCT/EP2019/062534, "Pharmaceutical Formulation" Dated Aug. 26, 2019.
International Preliminary Report on Patentability for International Application No. PCT/EP2019/062534, "Pharmaceutical Formulation" Dated Nov. 17, 2020.
Imigran 10mg Nasal Spray, Summary of Product Characteristics updated Feb. 26, 2015, https://www.medicines.org.uk/emc/product/2214/smpc.
Migran Injection, Subject, Summary of Product Characteristics updated May 4, 2018, https://www.medicines.org.uk/emc/product/944/smpc.
Imigran Tablets 50 mg, Summary of Product Characteristics updated Oct. 6, 2020, https://www.medicines.org.uk/emc/product/945/smpc.
Imigran Tablets 50 mg, Summary of Product Characteristics updated Oct. 3, 2016, https://www.medicines.org.uk/emc/product/945/smpc.
Manfredi, P.L., et al., "Sumatriptan for Headache Caused by Head and Neck Cancer", Headache 2000; 40:758-760.
Harding, S.E., et al., "Molecular Weidht Determination of Polysaccharides", Advances in Carbohydrate Analysis, 1991, vol. 1, pp. 69-73.
Martinsen, A., et al., "Comparision of Different Methods for Determination of Molecular Weight and Molecular Weight Distribution of Alginates", Carbohydrate Polymers 15 (1991) 171-193.
Notice of Allowance for U.S. Appl. No. 16/607,892 "Pharmaceutical Formulation" dated Oct. 1, 2021.
Non-Final Office Action for U.S. Appl. No. 17/054,941 "Pharmaceutical Formulation" dated Dec. 13, 2021.
Non-Final Office Action for U.S. Appl. No. 17/054,945 "Pharmaceutical Formulation" dated Dec. 13, 2021.
Third Party Observation for EP Application No. 3793517 "Pharmaceutical Formulation" dated Aug. 23, 2021.
Non-Final Office Action for U.S. Appl. No. 17/215,963 "Pharmaceutical Formulation" dated Apr. 13, 2022.
Light, M.K., et al., The Marijuana Policy Group, Market Size and Demand for Marijuana in Colorado, Prepared for the Colorado Department of Revenue, http://www.cannabisconsumer.org/uploads/9/7 /9/6/97962014/market size and demand study, Jul. 9, 2014%5B1%5D.pdf.
Rawas-Qalaji, et al., "Fast-disintegrating Sublingual Tablets: Effect of Epinephrine Load on Tablet Characteristics", AAPS PharmSciTech 2006; 7 (2) Article 41.
Non-Final Office Action for U.S. Appl. No. 17/054,945 "Pharmaceutical Formulation" dated Dec. 20, 2021.
International Preliminary Report on Patentability for international application No. PCT/EP2020/072894, entitled "Film Formulation Comprising Carriers," dated Feb. 24, 2022.
International Search Report for international application No. PCT/EP2020/072894, entitled "Film Formulation Comprising Carriers," dated Oct. 26, 2020.
Written Opinion for international application No. PCT/EP2020/072894, entitled "Film Formulation Comprising Carriers," dated Oct. 26, 2020.
International Search Report for international application No. PCT/EP2020/073940, entitled "Film Formulation Comprising Carriers," dated Dec. 6, 2020.
Written Opinion for international application No. PCT/EP2020/073940, entitled "Pharmaceutical Formulation," dated Dec. 6, 2020.
International Preliminary Report on Patentability for international application No. PCT/EP2020/073940, entitled "Film Formulation Comprising Carriers," date of issuance: Mar. 1, 2022.
Klaria Pharma Holding AB, Experimental Report filed on Jul. 28, 2020 in relation to European patent application No. 17804124.0.
Non-Final Office Action for U.S. Appl. No. 17/457,460 "Pharmaceutical Formulation" dated Jun. 22, 2023.
Alayoubi, A., et al., "Development of a fast dissolving film of epinephrine hydrocholoride as a potential anaphylactic treatment for pediatrics", harm Dev Technol, Jan. 6, 2016, 7 pages.
Non-Final Office Action for U.S. Appl. No. 17/054,945, "Pharmaceutical Formulation", dated Apr. 20, 2023.
Non-Final Office Action for U.S. Appl. No. 17/054,941 "Pharmaceutical Formulation" dated Apr. 27, 2023.

(56) References Cited

OTHER PUBLICATIONS

Final Office Action for U.S. Appl. No. 17/054,941 "Pharmaceutical Formulation" dated Aug. 2, 2022.
Dixit, et al., "Iontophoresis—An Approach for Controlled Drug Delivery: A Review", Current Drug Delivery, Apr. 1-10, 2007.
Final Office Action for U.S. Appl. No. 17/054,945 "Pharmaceutical Formulation" dated Aug. 26, 2022.
Notice of Allowance Action for U.S. Appl. No. 17/054,945 "Pharmaceutical Formulation" dated Feb. 6, 2024.
Non-Final Office Action received for U.S. Appl. No. 18/359,317, mailed on Oct. 9, 2024, 14 pages.
Non-Final Office Action received for U.S. Appl. No. 18/410,212, mailed on Aug. 28, 2024, 13 pages.

PHARMACEUTICAL FORMULATION

RELATED APPLICATIONS

This application is a continuation of U.S. application Ser. No. 17/215,963, filed Mar. 29, 2021, which is a continuation of U.S. application Ser. No. 16/349,840, filed Nov. 14, 2017, which is the U.S. National Stage Application of International Application No. PCT/EP2017/079217 filed on Nov. 14, 2017, published in English, which claims priority under 35 U.S.C. § 119 or 365 to GB Application No. 1619324.5, filed Nov. 15, 2016. The entire teachings of the above applications are incorporated herein by reference.

FIELD OF THE INVENTION

The present invention relates to a film comprising an alginate salt of a monovalent cation or a mixture of alginate salts containing at least one alginate salt of a monovalent cation, and a triptan or a pharmaceutically acceptable salt or solvate thereof. The present invention further relates to methods for manufacturing such a film, and the use of such a film in the treatment of disease, in particular migraine with or without aura, cluster headache, or trigeminal neuralgia.

BACKGROUND TO THE INVENTION

Sumatriptan is a specific vascular 5-hydroxytryptamine-1 (5-$HT_1$) receptor agonist. It belongs to the more general class of 5-$HT_1$ receptor agonists based on the monoamine alkaloid tryptamine, which are known as triptans. Other triptans include zolmitriptan, naratriptan, rizatriptan, almotriptan, eletriptan, frovatriptan, donitriptan and avitriptan. The vascular 5-$HT_1$ receptor is predominantly found in cranial blood vessels and mediates vasoconstriction. Dilation and/or oedema formation in extracranial and intracranial vessels are thought to be the underlying mechanism of migraine. It is also believed that sumatriptan and other triptans may inhibit trigeminal nerve activity, which additionally may contribute to the anti-migraine action of these compounds in humans [1].

Sumatriptan has been marketed in the EU since 1991 and in the USA since 1993 for the treatment of migraine and is today available in several administration forms, including: subcutaneous injection; oral tablets; transdermal skin patches; suppositories; and nasal spray. Absorption, bioavailability and time to effect differ between the different delivery formulations but the pharmacokinetics and metabolism of sumatriptan when it has reached the circulation is similar between all administration forms and has been well described and documented [2]. After intranasal administration, sumatriptan is absorbed into the bloodstream, with a maximum plasma concentration occurring within 1-1.5 hours. After a 20 mg dose, the mean maximum concentration has been reported as 12.9 ng/mL, with mean intranasal bioavailability of 15.8% [3].

Since sumatriptan has been used for the treatment of migraine for many years there is an extensive knowledge regarding its risks. Adverse events are generally of mild or moderate severity, of short duration, and more common with subcutaneous administration and higher doses of oral and intranasal sumatriptan than with other dose and route combinations [3].

The recommended dosage of sumatriptan for adults is between 10 and 100 mg sumatriptan per migraine attack. One of the most commonly used clinical end-points to determine the success of a migraine treatment is the proportion of patients who are "pain-free at two hours" after taking medication; this analysis may be referred to as the "PF2" assessment [3].

Subcutaneous administration is the most effective route of administration of sumatriptan, with pain reduced from moderate or severe to none within two hours of subcutaneous administration in almost 6 out of 10 people (60%) taking 6 mg sumatriptan, compared to approximately 1 out of 7 (15%) taking placebo [3]. The most effective oral dose is 100 mg and for the nasal spray 20 mg. The suppository formulation of sumatriptan (25 mg) also shows comparatively good efficacy [3].

However, both subcutaneous and rectal administration of sumatriptan is relatively invasive and can be unpleasant for patients. On the other hand, in migraine patients nasal administration of sumatriptan has not been completely successful, with disappointing efficacy compared to rectal administration and even oral tablets [3]. The relatively modest efficacy of nasal sprays in migraine patients could be a function of variability in patient application technique which may also contribute to lower acceptance of this dosage form. An additional aspect of low acceptance of nasal sprays in migraine patients is that some migraine patients report that nasal sprays increase the incidence of vomiting if the patient is already nauseous [4]. Tablet-based oral formulations are also known to be poorly tolerated by nauseous patients.

Finally, nasal sprays may not achieve the plasma concentrations required for effective migraine pain relief. It appears that for the most reliable migraine-relieving effect, plasma levels over 9.44 ng/mL [5] need to be achieved within 60 minutes after dosing [6]. Thus any dosing method of sumatriptan that does not achieve a plasma level of sumatriptan exceeding roughly 10 ng/mL, or only achieves this adequate plasma level after the first 60 minutes from administration, may not exhibit efficacy in the maximum number of patients possible.

Therefore, no formulation of sumatriptan is currently available which can be administered in a non-invasive fashion, is compatible with nauseous patients and which results in acceptable bioavailability and blood plasma concentrations of sumatriptan with low variability between patients.

SUMMARY OF THE INVENTION

The present invention is based on the unexpected finding that formulations of triptans such as sumatriptan, or pharmaceutically acceptable salts thereof, in a film suitable for administration to an oral cavity can provide a desirable balance of properties for use in the treatment of migraine and related diseases. The properties of a triptan-containing film compare favourably with those of other triptan-containing formulations, for example subcutaneous, suppository, oral tablet or nasal spray formulations. In particular, it is a surprising finding of the present invention that when films as herein defined containing sumatriptan are administered to patients, significantly more of those patients reach the desirable plasma level of above 10 ng/mL sumatriptan within 60 minutes of treatment than patients adminstered the commercially available nasal spray of sumatriptan.

Hence, the invention provides for the first time a film suitable for administration to an oral cavity comprising a triptan such as sumatriptan, or a pharmaceutically acceptable salt or solvate thereof, and its use in the treatment of patients suffering from migraine and related diseases.

In one aspect, the present invention provides an film suitable for administration to an oral cavity comprising:
(i) an alginate salt of a monovalent cation or a mixture of alginate salts containing at least one alginate salt of a monovalent cation; and
(ii) a triptan or a pharmaceutically acceptable salt thereof.

In another aspect, the present invention provides a film according to the invention for use in the treatment of a human patient.

In another aspect, the present invention provides a film according to the invention for use in the treatment of migraine with or without aura, cluster headache, or trigeminal neuralgia in a human patient.

In a further aspect, the present invention provides a method of treating a disease in a human patient, wherein said method comprises administration of at least one film according to the invention to the human patient, wherein the disease to be treated is selected from the group consisting of migraine with or without aura, cluster headache, and trigeminal neuralgia.

In another aspect, the present invention provides the use of a film according to the invention for the manufacture of a medicament for the treatment of a disease in a human patient, wherein the disease to be treated is selected from the group consisting of migraine with or without aura, cluster headache, and trigeminal neuralgia.

In another aspect, the present invention provides a method of manufacturing a film according to the invention, said method comprising the following steps:
(a) mixing the triptan or a pharmaceutically acceptable salt thereof and, optionally, at least one buffering component in water;
(b) adjusting the pH of the solution to the desired level by addition of an appropriate acid or base, typically a diluted aqueous acid or alkali, and preferably adjusting the pH of the solution to from 3.25 to 12.0;
(c) optionally, adding further water and/or one or more plasticizers under further mixing;
(d) adding the alginate salt of monovalent cation under suitable conditions to result in the formation of a viscous cast;
(e) pouring the cast onto a surface and spreading the cast out to the desired thickness;
(f) drying the cast layer, typically at a temperature of from 45 to 70° C. until the residual water content of the film is from 5 to 15% by weight and a solid film is formed; and
(g) optionally, cutting the solid film into pieces of the desired size, further optionally placing these pieces into pouches, preferably wherein the pouches are made from PET-lined aluminium, sealing the pouches and further optionally, labelling them.

DETAILED DESCRIPTION OF THE INVENTION

Figure 1:
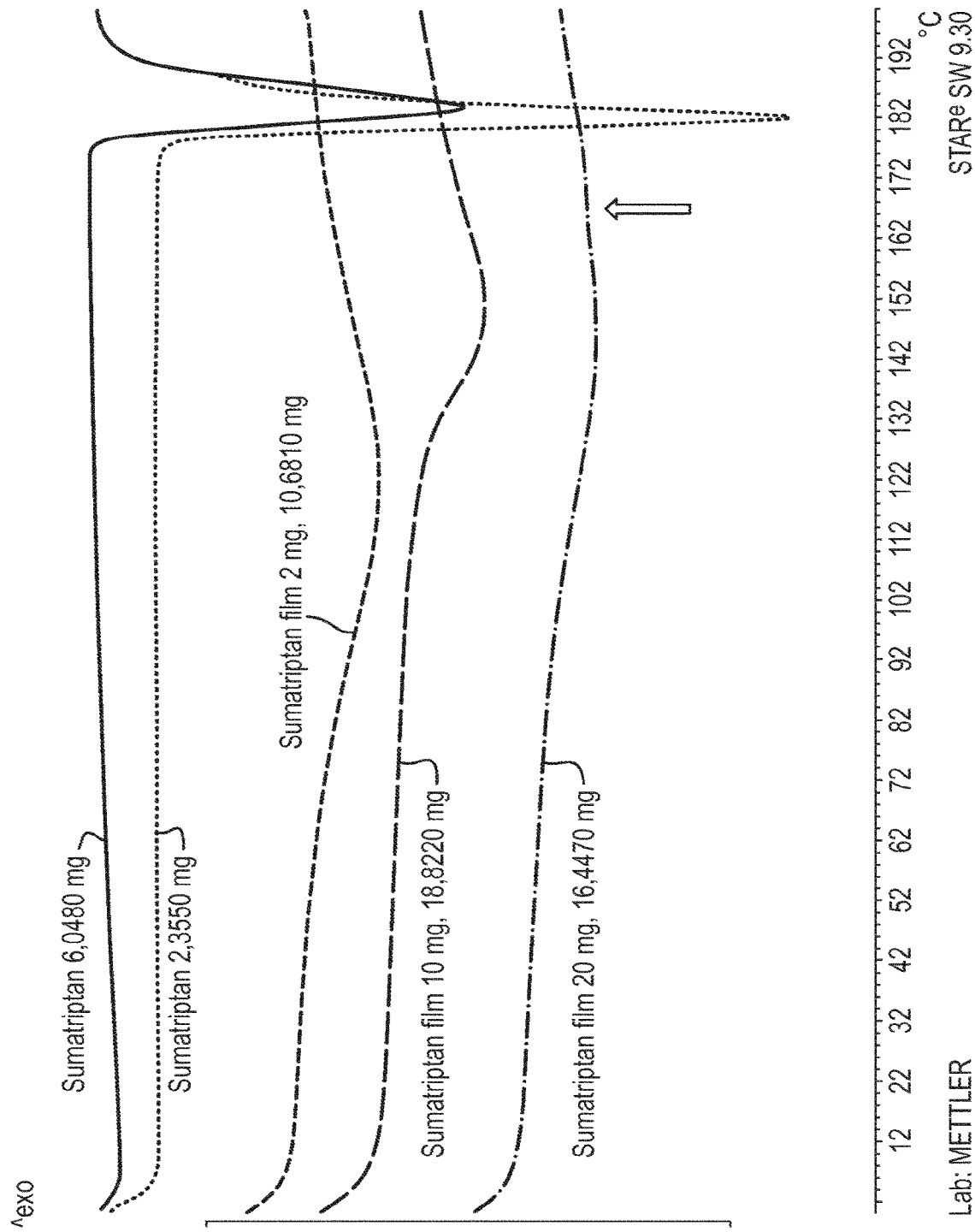
FIG. 1: Differential scanning calorimetry curves for sumatriptan and films containing 2 mg, 10 mg and 20 mg sumatriptan. A slight peak (indicated with an arrow) on the curve obtained from the 20 mg sumatriptan film, and not present on the curves from the 2 mg and 10 mg films, suggests the presence of sumatriptan in crystal form in the 20 mg film.

The present invention is concerned with a film, suitable for administration to an oral cavity, which can be used for delivery of a triptan or a pharmaceutically acceptable salt thereof to a human patient. Such a film may also be referred to as an oral dissolvable film (ODF) and/or an oral transmucosal film (OTF). The film is typically an alginate film which is applied by the patient to the mucosa of the oral cavity. The film is bioadhesive and adheres to the surface of the oral cavity upon application. After application, the alginate film begins to dissolve, releasing the triptan active ingredient. The present invention is useful in particular in the treatment of migraine with or without aura, cluster headache, or trigeminal neuralgia. For the avoidance of doubt, all alternative and preferred features relating to the film per se apply equally to the use of said film in the treatment of disease in a human patient. The term "oral cavity" is understood to mean the cavity of the mouth, and includes the inner upper and lower lips, all parts of the inner cheek, the sublingual area under the tongue, the tongue itself, as well as the upper and lower gums and the hard and soft palate. The term "oral mucosa" is understood to mean the mucous membrane lining the inside of the mouth, and includes (but does not exclusively refer to) mucosa in the buccal, labial, sublingual, ginigival or lip areas, the soft palate and the hard palate.

Films of the Present Invention

The present invention provides a film suitable for administration to an oral cavity comprising:
(i) an alginate salt of a monovalent cation or a mixture of alginate salts containing at least one alginate salt of a monovalent cation; and
(ii) a triptan or a pharmaceutically acceptable salt thereof.

The function of said alginate salt of a monovalent cation or mixture of alginate salts containing at least one alginate salt of a monovalent cation within the film is to act as a film-forming agent. As used herein, the term "film-forming agent" refers to a chemical or group of chemicals that form a pliable, cohesive and continuous covering when applied to a surface.

Alginate, the salt of alginic acid, is a linear polysaccharide naturally produced by brown seaweeds (Phaeophyceae, mainly *Laminaria*). Typically the alginate employed in the present invention comprises from 100 to 3000 monomer residues linked together in a flexible chain. These residues are of two types, namely β-(1,4)-linked D-mannuronic acid (M) residues and α-(1,4)-linked L-guluronic acid (G) residues. Typically, at physiological pH, the carboxylic acid group of each residue in the polymer is ionised. The two residue types are epimers of one another, differing only in their stereochemistry at the C5 position, with D-mannuronic acid residues being enzymatically converted to L-guluronic acid residues after polymerization. However, in the polymer chain the two residue types give rise to very different conformations: any two adjacent D-mannuronic acid residues are $^4C_1$-diequatorially linked whilst any two adjacent L-guluronic acid residues are $^4C_1$-diaxially linked, as illustrated in Formula (I) below.

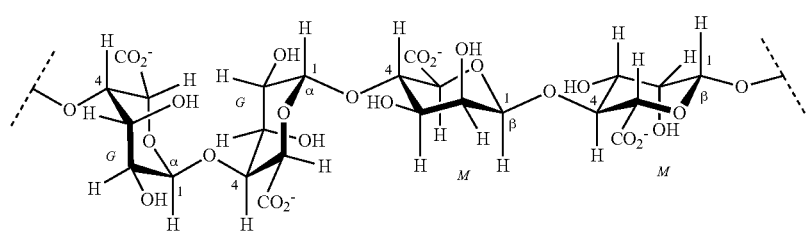

Formula (I)

Typically in the alginate polymer, the residues are organised in blocks of identical or strictly alternating residues, e.g. MMMMM ..., GGGGG ... or GMGMGM .... Different monovalent and polyvalent cations may be present as counter ions to the negatively-charged carboxylate groups of the D-mannuronic acid and L-guluronic acid residues of the alginate polymer. Typically, the film comprises an alginate salt wherein the counter ions of the alginate polymer are monovalent cations. The cations which are the counterions of a single alginate polymer molecule may all be the same as one another or may be different to one another. Preferably, the counterions of the alginate polymer are selected from the group consisting of $Na^+$, $K^+$ and $NH_4^+$. More preferably, the counterions of the alginate polymer are $Na^+$. Alternatively, the film may comprise a mixture of alginate salts containing at least one alginate salt of a monovalent cation. The mixture of alginate salts may comprise an alginate salt of a cation selected from the group consisting of $Na^+$, $K^+$ and $NH_4^+$.

Typically, the film comprises an alginate composition which has a dynamic viscosity, as measured on a 10% aqueous solution (w/w) thereof at a temperature of 20° C. with a Brookfield LVF viscometer (obtained from Brookfield Engineering Laboratories, Inc.), using a spindle No. 2 at a shear rate of 20 rpm, of 100-1000 mPa·s, or 200-800 mPa·s, or 300-700 mPa·s.

Preferably, the film comprises an alginate composition having a mean guluronate (G) content of from 50 to 85%, more preferably from 60 to 80%, and most preferably from 65 to 75% by weight. Preferably, the film comprises an alginate composition having a mean maluronate (M) content of from 15 to 50%, more preferably from 20 to 40%, and most preferably from 25 to 35% by weight. Preferably, the film comprises an alginate composition having a mean molecular weight ranging from 30,000 g/mol to 90,000 g/mol, such as from 35,000 g/mol to 85,000 g/mol, or from 40,000 g/mol to 70,000 g/mol, or from 40,000 g/mol to 50,000 g/mol. Preferably, the film comprises an alginate composition having a mean guluronate (G) content of from 50 to 85%, a mean maluronate (M) content of from 15 to 50%, and a mean molecular weight ranging from 30,000 g/mol to 90,000 g/mol. More preferably, the film comprises an alginate composition having a mean guluronate (G) content of from 60 to 80%, a mean maluronate (M) content of from 20 to 40%, and a mean molecular weight ranging from 30,000 g/mol to 90,000 g/mol. Most preferably, the film comprises an alginate composition having a mean guluronate (G) content of from 65 to 75%, a mean maluronate (M) content of from 25 to 35%, and a mean molecular weight ranging from 30,000 g/mol to 90,000 g/mol.

The alginate salt of a monovalent cation or the mixture of alginate salts containing at least one alginate salt of a monovalent cation may be the sole film-forming agent present in the film. Alternatively, the film may comprise one or more further film-forming agents in addition to the alginate salt of a monovalent cation or the mixture of alginate salts containing at least one alginate salt of a monovalent cation.

It is preferred that the film comprises Protanal® LFR 5/60 or Protanal® LF 10/60 (both commercially available sodium alginate products from FMC BioPolymer) as the alginate salt. Protanal® LFR 5/60 is a low molecular weight and low viscosity sodium alginate extracted from the stem of *Laminaria hyperborean*. Protanal® LF 10/60 is a sodium alginate having a G/M % ratio of 65-75/25-35 and a viscosity of from 20-70 mPas as measured on a 1% aqueous solution thereof at a temperature of 20° C. with a Brookfield LVF viscometer, using a spindle No. 2 at a shear rate of 20 rpm. Protanal® LF 10/60 has both a higher mean molecular weight and a higher viscosity than Protanal® LFR 5/60.

Without wishing to be bound by any particular theory, a film comprising a higher viscosity alginate salt is believed to have a longer residence time (i.e. dissolving time) after application to the oral cavity via adhesion to a mucous membrane of said cavity than a film comprising a lower viscosity alginate salt of a similar thickness. It is contemplated that the viscosity of the alginate composition within the film may be adjusted by mixing any number of alginates having different viscosities. Typically, a film of about 1 mm thickness comprising Protanal® LFR 5/60 as the sole alginate component has a residence time of approximately 3-10 minutes after adhesion to a mucous membrane of the oral cavity. In contrast, a film of about 1 mm thickness comprising Protanal® LF 10/60 as the sole alginate component has a residence time of approximately 30 minutes after adhesion to a mucous membrane of the oral cavity.

Therefore, if a long residence time of the film within the oral cavity is desired, it is generally preferred that the film comprises Protanal® LF 10/60 as the alginate salt. However, compared to films comprising Protanal® LFR 5/60 as the alginate salt, films comprising Protanal® LF 10/60 as the alginate salt typically exhibit inferior adhesion properties when applied to a mucous membrane of the oral cavity. More generally, it is believed that film-forming agents having longer average chain lengths exhibit poorer adhesion to mucosa than film-forming agents having shorter average chain lengths. Without wishing to be bound by any particular theory, it is believed that better mucoadhesion of a film to the mucous membrane of the oral cavity enables a more efficient delivery of any active ingredients contained within the film to their site of action. Therefore, if a long residence time of the film within the oral cavity is not particularly necessary, it may be preferable to use Protanal® LFR 5/60 as the alginate salt.

It is particularly preferred that the film comprises Protanal® LFR 5/60 as the alginate salt.

The film may also comprise a film-forming agent other than the alginate salt of a monovalent cation or the mixture of alginate salts containing at least one alginate salt of a monovalent cation. Such other film-forming agents include agents such as poly(vinyl pyrrolidone) (PVP), pullulan, hydroxypropyl methylcellulose (HPMC), other cellulose-based film-forming agents, and so forth. However, if any other film-forming agent is present in the film in addition to the alginate salt of a monovalent cation or the mixture of alginate salts containing at least one alginate salt of a monovalent cation, then typically the alginate salt of a monovalent cation or the mixture of alginate salts containing at least one alginate salt of a monovalent cation will be present in the film in excess over any other film-forming agent present. Preferably, the ratio (by weight) of the alginate salt of a monovalent cation or the mixture of alginate salts containing at least one alginate salt of a monovalent cation present in the film to the combined total of all other film-forming agents (such as PVP, pullulan and/or HPMC) present in the film is 1:1 or greater, or 2:1 or greater, or 3:1 or greater, or 4:1 or greater, or 5:1 or greater, or 10:1 or greater, or 20:1 or greater, or 50:1 or greater, or 100:1 or greater, or 500:1 or greater, or 1000:1 or greater, or 10000:1 or greater. Preferably, the alginate salt of a monovalent cation or the mixture of alginate salts containing at least one alginate salt of a monovalent cation will constitute at least 50% by weight of the total of the film-forming agents present in the film, more preferably at least 60% by weight, at least 70% by weight, at least 80% by weight, at least 90% by weight, at least 95% by weight, at least 98% by weight, at least 99% by weight, at least 99.5% by weight, at least 99.9% by weight, at least 99.95% by weight, or at least 99.99% by weight of the total of the film-forming agents present in the film.

Preferably, the alginate salt of a monovalent cation or the mixture of alginate salts containing at least one alginate salt of a monovalent cation is substantially the only film-forming agent present in the film. More preferably, the alginate salt of a monovalent cation or the mixture of alginate salts containing at least one alginate salt of a monovalent cation is the only film-forming agent present in the film. Alternatively, the film preferably does not comprise any, or substantially any, poly(vinyl pyrrolidone). Alternatively, the film preferably does not comprise any, or substantially any, pullulan.

As used herein, a reference to a film that does not comprise "substantially any" of a specified component refers to a film that may contain trace amounts of the specified component, provided that the specified component does not materially affect the essential characteristics of the film. Typically, therefore, a film that does not comprise substantially any of a specified component contains less than 5 wt % of the specified component, preferably less than 1 wt % of the specified component, most preferably less than 0.1 wt % of the specified component.

It is a finding of the present invention that the use of an alginate salt of a monovalent cation or a mixture of alginate salts containing at least one alginate salt of a monovalent cation as the film-forming agent has benefits over the use of alternative film-forming agents, such as PVP, pullulan and/or HPMC. In particular, the use of alginate as the primary film-forming agent ensures that the films of the present invention have superior adhesive properties over films comprising primarily other film-forming agents such as PVP, pullulan and/or HPMC. The films of the present invention are bioadhesive; that is to say that the films of the present invention can firmly adhere to a moist surface (i.e. mucosa) in the oral cavity of a mammal subject before it has fully dissolved. Films in which alginate is not the primary film-forming agent do not generally have this desirable property. A further advantageous finding of the present invention is that the choice of alginate as the primary film-forming agent enables therapeutically effective doses of an active pharmaceutical ingredient (e.g., sumatriptan) to be loaded into the films whilst retaining homogeneity and other desirable physical properties of the films.

Typically, the film comprises from 25% to 99% by weight of the alginate salt of a monovalent cation or the mixture of alginate salts containing at least one alginate salt of a monovalent cation, preferably from 25% to 88% by weight, more preferably from 30% to 86% by weight, still more preferably from 35% to 75% by weight, and most preferably from 35% to 45% by weight.

The film according to the present invention may also contain a residual water content. Typically, the film comprises from 0% to 20% by weight of residual water. More typically, the film comprises from 5% to 15% by weight of residual water. Preferably, the film comprises from 9% to 11% by weight of residual water. Most preferably, the film comprises about 10% by weight of residual water.

The film according to the present invention also comprises an active pharmaceutical ingredient (API) which is a triptan or a pharmaceutically acceptable salt thereof. The triptan or a pharmaceutically acceptable salt thereof is present in a therapeutically effective amount in the film. Typically, the API is a triptan. Alternatively, the API may be a pharmaceutically acceptable salt of a triptan. The API may be a pharmaceutically acceptable polymorph, co-crystal, hydrate or solvate of a triptan or a pharmaceutically acceptable salt thereof. Typically, the triptan is selected from the group selected from: sumatriptan, zolmitriptan, naratriptan, rizatriptan, almotriptan, eletriptan, frovatriptan, donitriptan and avitriptan. The structures of these triptans are provided in Formulae (II) to (X) below.

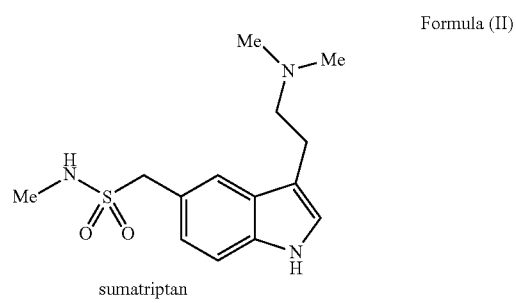

Formula (II)

sumatriptan

Formula (III)

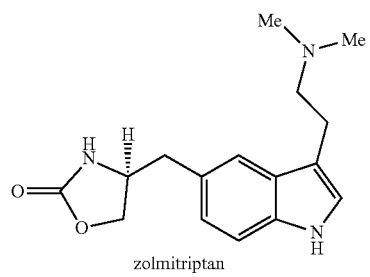
zolmitriptan

Formula (IV)

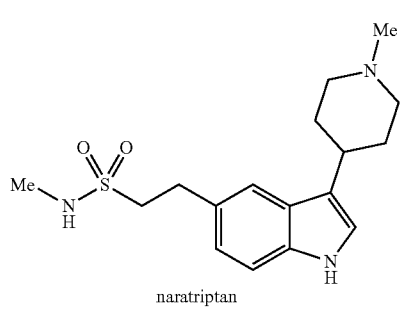
naratriptan

Formula (V)

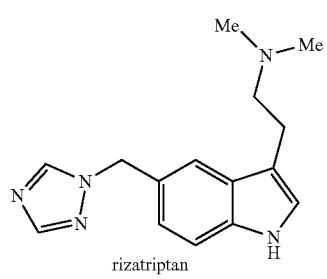
rizatriptan

Formula (VI)

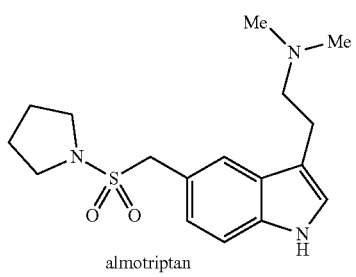
almotriptan

Formula (VII)

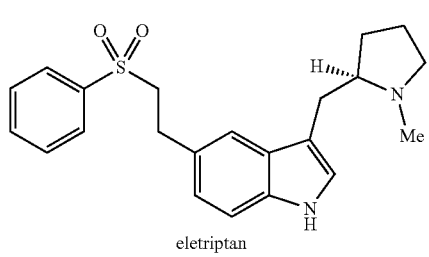
eletriptan

Formula (VIII)

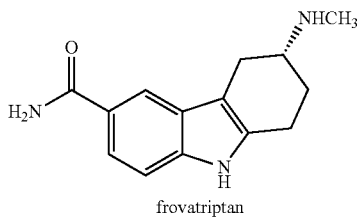
frovatriptan

Formula (IX)

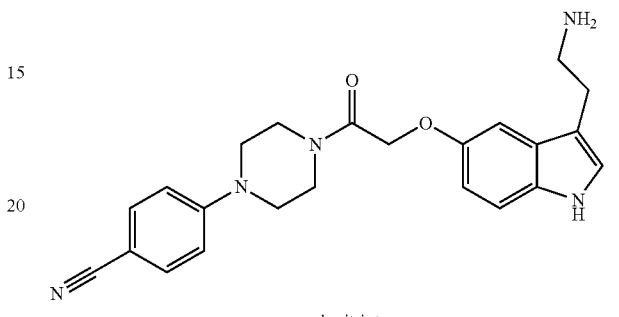
donitriptan

Formula (X)

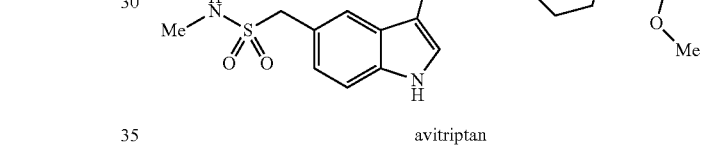
avitriptan wherein -Me refers to a methyl (i.e. —CH$_3$) substituent.

Typically, the pharmaceutically acceptable salt of the triptan is selected from the group consisting of succinate, tartrate, citrate, fumarate, malonate, maleate, adipate, di-mesylate, sulfate, benzenesulfonate, hydrochloride, and phosphate salts of the triptan. Preferred salt forms of triptans include dicarboxylic acid salts, hydrochloric acid salts, phosphoric acid salts, sulfuric acid salts or benzenesulfonic acid salts of the triptan. Most preferably, the pharmaceutically acceptable salt of the triptan is the phosphoric acid salt of the triptan.

Preferably, the triptan is sumatriptan, zolmitriptan or naratriptan, or a pharmaceutically acceptable salt thereof. Most preferably, the triptan is sumatriptan or a pharmaceutically acceptable salt thereof.

Preferred salt forms of sumatriptan include dicarboxylic acid salts, hydrochloric acid salts, phosphoric acid salts, sulfuric acid salts or benzenesulfonic acid salts of sumatriptan. Most preferably, the pharmaceutically acceptable salt of sumatriptan is the phosphoric acid salt of sumatriptan.

The API may be present within the film in varying amounts. Typically, the film comprises from 0.001% to 75% by weight of the API, preferably from 2% to 50% by weight of the API, more preferably from 4% to 40% by weight of the API, yet more preferably from 11% to 35% by weight of the API, still more preferably from 15% to 35% by weight of the API and most preferably about 30% by weight of the API.

Generally, the triptan or a pharmaceutically acceptable salt thereof is the only API present in the film. However, the film may alternatively comprise one or more further active pharmaceutical ingredients in addition to the triptan or a pharmaceutically acceptable salt thereof. Preferably, the triptan or a pharmaceutically acceptable salt thereof is sumatriptan or a pharmaceutically acceptable salt thereof.

Preferably, the film comprises from 25% to 99% by weight of the alginate salt of a monovalent cation or the mixture of alginate salts containing at least one alginate salt of a monovalent cation, from 0% to 20% by weight of water, and from 0.001% to 75% by weight of the API. More preferably, the film comprises from 30% to 86% by weight of the alginate salt of a monovalent cation or the mixture of alginate salts containing at least one alginate salt of a monovalent cation, from 5% to 15% by weight of water, and from 4% to 40% by weight of the API. Even more preferably, the film comprises from 35% to 75% by weight of the alginate salt of a monovalent cation or the mixture of alginate salts containing at least one alginate salt of a monovalent cation, from 9% to 11% by weight of water, and from 15% to 35%, by weight of the API.

A film according to the present invention may optionally further comprise other components in addition to the API, water and the film-forming agent. Typically, a film according to the present invention further comprises one or more of the following:
   (i) at least one pharmaceutically acceptable solvent;
   (ii) at least one buffering component;
   (iii) at least one excipient; and
   (iv) at least one acidifying agent or basifying agent.

The film may additionally comprise any pharmaceutically acceptable solvent. Such a solvent may be a non-aqueous solvent, or a combination of water and a non-aqueous solvent. Examples of non-aqueous solvents should be non-toxic and include, but are not limited to, ethanol, acetone, benzyl alcohol, diethylene glycol monoethyl ether, glycerine, hexylene glycol, isopropyl alcohol, polyethylene glycols, methoxypolyethylene glycols, diethyl sebacate, dimethyl isosorbide, propylene carbonate, and dimethyl sulfoxide.

The film may additionally comprise any suitable buffering component. A "buffering component", as defined herein, refers to any chemical entity, which when dissolved in solution, enables said solution to resist changes in its pH following the subsequent addition of either an acid or a base. A suitable buffering component for use in the film of the present invention would be a buffering component which is an effective buffer within a pH range of from 3.25 to 12.0, preferably within a pH range of from 3.5 to 10.0, more preferably within a pH range of from 4.5 to 5.5 and most preferably at a pH of about 5.0. Examples of suitable buffering components include, but are not limited to: phosphates, sulfates, citrates and acetates. Preferably, the buffer is a salt of a monovalent cation, such as sodium, potassium or ammonium salts. It is particularly preferred that the film additionally comprises a buffering component which is sodium dihydrogen phosphate.

Typically, the film comprises from 0.1% to 10% by weight of the buffering component, preferably 0.2% to 6% by weight, more preferably from 0.3% to 4% by weight, and most preferably from 1.5% to 4% by weight.

The film may additionally comprise any suitable excipient, such as one or more fillers or plasticizers. The film may comprise both a plasticizer and a filler. Alternatively, the film may comprise just one of a plasticizer or a filler. It is preferred that the film comprises a plasticizer. Under some circumstances it may be desirable that the film does not comprise a filler. It is particularly preferred that the film comprises a plasticizer but does not comprise a filler. The film may additionally include a taste-masking agent or a flavouring agent. The taste-masking agent may be a sweetener.

The plasticizer, when present, may be selected from the group consisting of polyethylene glycol, glycerol, sorbitol, xylitol and a combination thereof. Typically, the film comprises a plasticizer which is selected from the group consisting of glycerol, sorbitol and a combination thereof. Preferably, the film comprises both glycerol and sorbitol as plasticizers. The film may comprise from 0% to 40% by weight of each plasticizer present, preferably from 5% to 30% by weight of each plasticizer, more preferably from 5% to 25% by weight of each plasticizer, and most preferably from 10% to 20% by weight of each plasticizer.

The filler, when present, may be e.g. microcrystalline cellulose or titanium dioxide. A suitable amount of filler may be from 0% to 20% by weight, e.g. from 0.1% to 10% by weight, of the total pharmaceutical composition. Preferably, if a filler is present, the filler is titanium dioxide. A preferred amount of titanium dioxide may be from 0.1% to 1% by weight of the total pharmaceutical composition, more preferably from 0.1% to 0.3% by weight of the total pharmaceutical composition.

The film may additionally comprise one or more further excipients. Suitable further excipients which may be included in the film include ethylenediaminetetraacetic acid (EDTA), citric acid, benzalkonium chloride, bisulfite, butylated hydroxyanisole (BHA), butylated hydroxytoluene (BHT), dimethyl sulfoxide (DMSO), menthol, oleic acid, Tween and ascorbic acid. Typically, the film may comprise EDTA. A suitable amount of EDTA may be from 0.0001% to 5% by weight of the total pharmaceutical composition, preferably from 0.001% to 2% by weight of the total pharmaceutical composition. Typically, the film may comprise citric acid. The concentration of citric acid in the film may be from 1 to 40 mM, preferably from 5 to 20 mM. Typically, the film may comprise benzalkonium chloride. A suitable amount of benzalkonium chloride may be from 0.001% to 0.05% by weight of the total pharmaceutical composition, preferably from 0.01% to 0.03% by weight of the total pharmaceutical composition, more preferably about 0.02% by weight of the total pharmaceutical composition. Typically, the film may comprise bisulfite. A suitable amount of bisulfite may be from 0.0001% to 5% by weight of the total pharmaceutical composition, preferably from 0.001% to 2.5% by weight of the total pharmaceutical composition. Typically, the film may comprise BHA. A suitable amount of BHA may be from 0.001% to 0.1% by weight of the total pharmaceutical composition, preferably from 0.02% to 0.04% by weight of the total pharmaceutical composition. Typically, the film may comprise BHT. A suitable amount of BHT may be from 0.001% to 0.05% by weight of the total pharmaceutical composition, preferably from 0.01% to 0.02% by weight of the total pharmaceutical composition. Typically, the film may comprise DMSO. A suitable amount of DMSO may be from 0.01% to 2% by weight of the total pharmaceutical composition, preferably from 0.3% to 0.5% by weight of the total pharmaceutical composition. Typically, the film may comprise menthol. A suitable amount of menthol may be from 0.01% to 1% by weight of the total pharmaceutical composition, preferably about 0.2% by weight of the total pharmaceutical composition. Typically, the film may comprise oleic acid. A suitable amount of oleic acid may be from 0.05% to 0.5% by weight of the total pharmaceutical composition, preferably from 0.2% to 0.3% by weight of the total pharmaceutical composition, more preferably about 0.25% by weight of the total pharmaceutical composition. Typically, the film may comprise Tween. A suitable amount of Tween may be from 0.01% to 0.5% by weight of the total pharmaceutical composition, preferably from 0.1% to 0.15% by weight of the total pharmaceutical composition, more preferably about 0.13% by weight of the total pharmaceutical composition. Typically, the film may comprise ascorbic acid. A suitable amount of ascorbic acid may be from 0.01% to 0.5% by weight of the total pharmaceutical composition, preferably from 0.1% to 0.3% by weight of the total pharmaceutical composition, more preferably about 0.2% by weight of the total pharmaceutical composition.

The film may additionally comprise an acidifying agent or a basifying agent. An "acidifying agent", as defined herein, refers to a chemical compound that alone or in combination with other compounds can be used to acidify a pharmaceutical composition. A "basifying agent", as defined herein, refers to a chemical compound that alone or in combination with other compounds can be used to basify a pharmaceutical composition. Preferably, the film may additionally comprise an acidifying agent. Typically, the film comprises an acidifying agent which is an acid having a $pK_a$ of 9.5 or less, more preferably having a $pK_a$ of 7.0 or less, and most preferably having a $pK_a$ of 5.0 or less. Examples of suitable acidifying agents include, but are not limited to: acetic acid, dehydro acetic acid, ascorbic acid, benzoic acid, boric acid, citric acid, edetic acid, hydrochloric acid, isostearic acid, lactic acid, nitric acid, oleic acid, phosphoric acid, sorbic acid, stearic acid, sulfuric acid, tartaric acid, and undecylenic acid. Preferably, the film comprises an acidifying agent which is phosphoric acid.

A film according to the present invention is produced via the drying of a film-forming solution (vide infra). Typically, a sufficient amount of acidifying agent or basifying agent is added to adjust the pH of the film-forming solution (before this is dried to form the film) to a pH of from 3.25 to 12.0, preferably a pH of from 3.5 to 10.0, more preferably a pH of from 4.5 to 5.5 and most preferably a pH of about 5.0.

Preferably, the film according to the present invention comprises from 25% to 99% by weight of the alginate salt of a monovalent cation or the mixture of alginate salts containing at least one alginate salt of a monovalent cation, from 0% to 20% by weight of water, from 0.001% to 75% by weight of the API, from 0.1% to 10% by weight of the buffering component, from 0% to 40% by weight of glycerol, from 0% to 40% by weight of sorbitol, and an acidifying agent. More preferably, the film according to the present invention comprises from 35% to 75% by weight of the alginate salt of a monovalent cation or the mixture of alginate salts containing at least one alginate salt of a monovalent cation, from 9% to 11% by weight of water, and from 15% to 35% by weight of the API, from 1.5% to 4% by weight of the buffering component, from 10% to 20% by weight of glycerol, from 10% to 20% by weight of sorbitol, and an acidifying agent.

Alternatively, the film according to the present invention consists of from 25% to 99% by weight of the alginate salt of a monovalent cation or the mixture of alginate salts containing at least one alginate salt of a monovalent cation, from 0% to 20% by weight of water, from 0.001% to 75% by weight of the API, from 0.1% to 10% by weight of the buffering component, from 0% to 40% by weight of glycerol, from 0% to 40% by weight of sorbitol, and an acidifying agent. Alternatively, the film according to the present invention consists of from 35% to 75% by weight of the alginate salt of a monovalent cation or the mixture of alginate salts containing at least one alginate salt of a monovalent cation, from 9% to 11% by weight of water, and from 15% to 35% by weight of the API, from 1.5% to 4% by weight of the buffering component, from 10% to 20% by weight of glycerol, from 10% to 20% by weight of sorbitol, and an acidifying agent.

A film according to the invention preferably has a thickness before drying of 200 to 2000 µm, more preferably from 300 to 1750 µm, even more preferably from 400 to 1500 µm, and most preferably about 1000 µm.

A film according to the invention preferably has a surface area on each of its two largest faces of from 0.1 to 20 $cm^2$, more preferably from 0.5 to 15 $cm^2$, even more preferably from 1 to 10 $cm^2$ and most preferably from 2 to 6 $cm^2$. Preferably, the surface area of each of the two largest faces of the film is about 3 $cm^2$.

The skilled person, having regard for the desired time of dissolution for a given application, will be able to select a suitable film thickness and surface area by simply preparing films of a range of different thicknesses and surface areas and testing the resultant films to measure the dissolution time.

The mechanical properties of a film according to the invention are very satisfactory. In particular, the film is flexible (i.e. it permits bending and folding without breaking), and has a high tensile strength. Importantly, the film of the present invention is not a gel, since the alginate polymer strands are not cross-linked with one another. The film of the invention is bioadhesive; that is to say that the film comprises a natural polymeric material (alginate) which can act as an adhesive. The film is adhesive to moist surfaces, such as mucosa. In particular, the film is adhesive to mucosa of the oral cavity, such as mucosa in the buccal, labial, sublingual, ginigival or lip areas, the soft palate and the hard palate.

The film according to the invention may be provided with printed text matter or printed images thereon, e.g. a brand name, a trade mark, a dosage indication or a symbol.

Administration and Uses of the Films in Treatment

In general, films of the present invention are administered to a human patients so as to deliver to the patient a therapeutically effective amount of the active pharmaceutical ingredient (API), preferably sumatriptan or a pharmaceutically acceptable salt thereof, contained therein.

As used herein, the term "therapeutically effective amount" refers to an amount of the API which is sufficient to reduce or ameliorate the severity, duration, progression, or onset of a disorder being treated, prevent the advancement of a disorder being treated, cause the regression of, prevent the recurrence, development, onset or progression of a symptom associated with a disorder being treated, or enhance or improve the prophylactic or therapeutic effect(s) of another therapy. The precise amount of API administered to a patient will depend on the type and severity of the disease or condition and on the characteristics of the patient, such as general health, age, sex, body weight and tolerance to drugs. It will also depend on the degree, severity and type of the disorder being treated. The skilled artisan will be able to determine appropriate dosages depending on these and other factors.

As used herein, the terms "treat", "treatment" and "treating" refer to the reduction or amelioration of the progression, severity and/or duration of a disorder being treated, or the amelioration of one or more symptoms (preferably, one or more discernible symptoms) of a disorder being treated resulting from the administration of a film according to the invention to a patient.

Typically, a film according to the present invention is provided for use in the treatment of a human patient. Preferably, the film according to the invention is provided for use in the treatment of migraine with or without aura, cluster headache, or trigeminal neuralgia in a human patient. More preferably, said film is provided for use in the treatment of migraine with or without aura in a human patient.

Typically, the human patient to be treated may also show signs of nausea in addition to suffering from one or more of migraine with or without aura, cluster headache and trigeminal neuralgia. The observed nausea in the human patient may be an acute bout of nausea, or alternatively may be symptomatic of a more chronic condition, such as any type of cancer. Therefore, it is preferred that the film according to the invention is for use in the treatment of migraine with or without aura, cluster headache, or trigeminal neuralgia in a human patient who (a) has been diagnosed with one or more types of cancer, and/or (b) is additionally receiving treatment for one or more types of cancer, and/or (c) is suffering from dysphagia from any cause.

Examples of cancers that a patient may be diagnosed with and/or receiving treatment for include, but are not limited to: Acute Lymphoblastic Leukaemia (ALL), Acute Myeloid Leukaemia (AML), Adrenocortical Carcinoma, Adrenal Cortex Cancer, AIDS-Related Cancers, AIDS-Related Lymphoma, Anal Cancer, Appendix Cancer, Astrocytomas, Atypical Teratoid/Rhabdoid Tumour, Basal Cell Carcinoma, Bile Duct Cancer, Bladder Cancer, Bone Cancer (including Ewing Sarcoma and Osteosarcoma and Malignant Fibrous Histiocytoma), Brain Tumours, Breast Cancer, Bronchial Tumours, Burkitt Lymphoma, Carcinoid Tumour, Cardiac Tumours, Cervical Cancer, Cholangiocarcinoma, Chordoma, Chronic Lymphocytic Leukaemia (CLL), Chronic Myelogenous Leukaemia (CML), Chronic Myeloproliferative Neoplasms, Colorectal Cancer, Craniopharyngioma, Cutaneous T-Cell Lymphoma, Ductal Carcinoma In Situ (DCIS), Embryonal Tumours, Endometrial Cancer, Ependymoma, Esophageal Cancer, Esthesioneuroblastoma, Extracranial Germ Cell Tumour, Extragonadal Germ Cell Tumour, Eye Cancer, Fallopian Tube Cancer, Gall Bladder Cancer, Gastrointestinal Carcinoid Tumours, Gastrointestinal Stromal Tumours (GIST), Gestational Trophoblastic Disease, Gliomas, Hairy Cell Leukaemia, Head and Neck Cancer, Hodgkin Lymphoma, Hypopharyngeal Cancer, Intraocular Melanoma, Kaposi Sarcoma, Kidney Cancer, Langerhans Cell Histiocytosis, Laryngeal Cancer, Leukaemia, Lip and Oral Cavity Cancer, Liver Cancer, Lung Cancer, Lymphoma, Melanoma, Merkel Cell Carcinoma, Malignant Mesothelioma, Multiple Endocrine Neoplasia Syndromes, Multiple Myeloma/Plasma Cell Neoplasms, Mycosis Fungoides, Myelodysplastic Syndromes, Myelodysplastic/Myeloproliferative Neoplasms, Chronic Myeloproliferative Neoplasms, Nasal Cavity and Paranasal Sinus Cancer, Nasopharyngeal Cancer, Neuroblastoma, Non-Hodgkin Lymphoma, Non-Small Cell Lung Cancer, Oral Cancer, Ovarian Cancer, Pancreatic Cancer, Pancreatic Neuroendocrine Tumours (Islet Cell Tumours), Papillomatosis, Paraganglioma, Paranasal Sinus and Nasal Cavity Cancer, Parathyroid Cancer, Penile Cancer, Pharyngeal Cancer, Pheochromocytoma, Pituitary Tumour, Plasma Cell Neoplasm/Multiple Myeloma, Pleuropulmonary Blastoma, Primary Central Nervous System (CNS) Lymphoma, Primary Peritoneal Cancer, Prostate Cancer, Retinoblastoma, Rhabdomyosarcoma, Salivary Gland Tumours, Sarcoma, Sézary Syndrome, Skin Cancer, Small Cell Lung Cancer, Small Intestine Cancer, Soft Tissue Sarcoma, Squamous Cell Carcinoma, Stomach Cancer, Testicular Cancer, Throat Cancer, Thymoma and Thymic Carcinoma, Thyroid Cancer, Urethral Cancer, Uterine Cancer, Endometrial and Uterine Sarcoma, Vaginal Cancer, Vascular Tumours, Vulvar Cancer, Waldenström Macroglobulinemia and Wilms Tumour.

Alternatively, the patient to be treated may be an elderly patient or a child. Both of these groups of patients are typically receiving more medication than the average, may be more susceptible to conditions which preclude the effective administration of oral tablets (e.g. nausea), and may not be able to self-medicate effectively (e.g. may find it difficult to administer the correct dose using a nasal spray).

Typically, the film is administered to the oral cavity of the patient. The film is preferably applied to an oral mucosa in the buccal or labial or sublingual areas or to the soft palate. The film is typically applied by the patient themselves.

The film is bioadhesive and adheres to the surface of the oral cavity upon application. After application, the alginate film begins to dissolve, releasing the active pharmaceutical ingredient. Typically, the film fully dissolves in a time period of from 0.1 to 60 minutes or more after application to the mucosa of the oral cavity. Preferably, the film fully dissolves in a time period of from 0.5 to 30 minutes, more preferably from 1 to 20 minutes, still more preferably from 3 to 10 minutes, and most preferably from 3 to 5 minutes after application to the mucosa of the oral cavity.

Without wishing to be bound by any particular theory, it is believed that as the film dissolves within the oral cavity, the active pharmaceutical ingredient which is concomitantly released may enter the bloodstream by one or both of two different routes: (a) via absorption across the oral mucosa directly into the bloodstream (the "oral transmucosal route"); and (b) via swallowing into the stomach and subsequent absorption across the epithelium of the intestines into the bloodstream. When the API is sumatriptan or a pharmaceutically acceptable salt thereof, typically a peak plasma concentration of between 5 and 50 ng/mL sumatriptan may be achieved, preferably between 10 and 30 ng/mL sumatriptan, and more preferably between 15 and 25 ng/mL. Preferably, the peak plasma concentration of sumatriptan in a patient exceeds 9.44 ng/mL, which is the target threshold plasma concentration of sumatriptan for relief of the symptoms of migraine with or without aura in a patient. This peak plasma concentration may be achieved within 180 minutes from adhesion of the film to the mucosa of the oral cavity, preferably within 120 minutes from adhesion, and most preferably within 75 minutes or 60 minutes from adhesion.

Typically, a single film is applied to the patient, generally to the mucosa of the oral cavity, at a given time. However, in some cases it may be desirable to apply two films simultaneously to achieve the correct dose for an individual patient. When the API is sumatriptan, the recommended dosage for adults is between 10 and 100 mg sumatriptan per migraine attack with the goal being efficacy that matches or exceeds that of current therapies as measured by the 'pain-free at two hours' (PF2) assessment [3]. In some cases it may be desirable to apply more than two films simultaneously to achieve the correct dose for an individual patient, for example, three, four, five, six, seven, eight, nine, ten or more.

The present invention also therefore provides a method of treating a disease in a human patient, wherein said method comprises administration of at least one film according to the invention to the oral cavity of the human patient, optionally wherein the disease to be treated is selected from the group consisting of migraine with or without aura, cluster headache, and trigeminal neuralgia, and preferably wherein the disease to be treated is migraine with or without aura.

The present invention also provides the use of a film according to the invention for the manufacture of a medicament for the treatment of a disease in a human patient, optionally wherein the disease to be treated is selected from the group consisting of migraine with or without aura, cluster headache, and trigeminal neuralgia, and preferably wherein the disease to be treated is migraine with or without aura.

The present invention also provides a product comprising one or more films according to the invention, and packaging. Each of the films may individually be wrapped within a pouch, or multiple films may be wrapped together within the same pouch. Optionally, said pouch is made from PET-lined aluminium. The product may further comprise instructions for use of the film. These instructions may contain information on the recommended frequency or timing of use of the film by a patient, how to use remove the film from its pouch or packaging, how to adhere the film to a mucous membrane, and where within the oral cavity to adhere the film to a mucous membrane.

Any film or films of the present invention may also be used in combination with one or more other drugs or pharmaceutical compositions in the treatment of disease or conditions for which the films of the present invention and/or the other drugs or pharmaceutical compositions may have utility.

The one or more other drugs or pharmaceutical compositions may be administered to the patient by any one or more of the following routes: oral, systemic (e.g. transdermal, intranasal, transmucosal or by suppository), or parenteral (e.g. intramuscular, intravenous or subcutaneous). Compositions of the one or more other drugs or pharmaceutical compositions can take the form of tablets, pills, capsules, semisolids, powders, sustained release formulations, solutions, suspensions, elixirs, aerosols, transdermal patches, bioadhesive films, or any other appropriate compositions. The choice of formulation depends on various factors such as the mode of drug administration (e.g. for oral administration, formulations in the form of tablets, pills or capsules are preferred) and the bioavailability of the drug substance.

Manufacture of the Films

The films according to the invention may be manufactured by preparing a film-forming solution by addition and mixing of the constituent components of the film, distributing this solution onto a solid surface, and permitting the solution to dry on the surface to form a film. To distribute a solution or composition onto a solid surface the solution or composition may simply be poured onto and/or spread evenly over the surface, e.g. by use of a draw-down blade or similar equipment.

An exemplary method includes the process steps of:
(a) mixing the API and, optionally, at least one buffering component in water;
(b) adjusting the pH of the solution to the desired level by addition of an appropriate acid or base, typically a diluted aqueous acid or alkali, and preferably adjusting the pH of the solution to from 3.25 to 12.0, more preferably from 3.5 to 10.0, even more preferably from 4.5 to 5.5, and most preferably adjusting the pH of the solution to about 5.0;
(c) optionally, adding further water and/or one or more plasticizers and/or one or more fillers under further mixing;
(d) adding the alginate salt of monovalent cation under suitable conditions to result in the formation of a viscous cast, e.g. by mixing for about 30 minutes or until a lump free dispersion is achieved;
(e) pouring the cast onto a surface, e.g. a plate, preferably a glass plate, and spreading the cast out to the desired thickness, typically by means of an applicator;
(f) drying the cast layer, typically at a temperature of from 45 to 70° C., and preferably from 55 to 60° C., until the residual water content of the film is from 0 to 20% by weight, preferably from 5 to 15% by weight, and more preferably from 9 to 11% by weight, and a solid film is formed; and
(g) optionally, cutting the solid film into pieces of the desired size, further optionally placing these pieces into pouches, preferably wherein the pouches are made from PET-lined aluminium, sealing the pouches and further optionally, labelling them.

In a particularly preferred example of this method, after the viscous cast is poured onto a surface, it is first spread out to a thickness of about 2 mm by means of an applicator with a slit height of about 2 mm, and is then subsequently spread out to a thickness of about 1 mm by means of an applicator with a slit height of about 1 mm.

Without wishing to be bound by any particular theory, it is believed that when only a one-step coating process is used, an unacceptably high variation was observed in the thickness of the resultant films produced. However, a lower dose weight variation was achieved using the two-step coating procedure, which appears to result in a more evenly distributed layer of cast/mass on the surface of the plate.

Typically, the alginate salt(s) are added to the API-containing water solution. Alternatively, the API and the alginate salt(s) are both dissolved together in solution. Alternatively, the API may be added to the alginate solution so as to give an emulsion or suspension of the API in the alginate solution. Alternatively, the film-forming composition of the invention may comprise both dissolved and non-dissolved active ingredients. For example, a film-forming composition may comprise a combination of active ingredient dissolved in the alginate solution and active ingredient suspended in the solution.

Additional API may be applied to the surface of the film before or after drying, e.g. as an aerosol spray onto a dry or wet film. An active ingredient may also be applied as a powder onto the surface of the film. A flavouring agent may additionally be applied in such a way.

The publications, patent publications and other patent documents cited herein are entirely incorporated by reference. Herein, any reference to a term in the singular also encompasses its plural. Where the term "comprising", "comprise" or "comprises" is used, said term may substituted by "consisting of", "consist of" or "consists of" respectively, or by "consisting essentially of", "consist essentially of" or "consists essentially of" respectively. Any reference to a numerical range or single numerical value also includes values that are about that range or single value. Any reference to a triptan also encompasses a physiologically acceptable salt thereof unless otherwise indicated. In particular, any reference to sumatriptan also encompasses a physiologically acceptable salt thereof. Any reference to alginate encompasses any physiologically acceptable salt thereof unless otherwise indicated. Unless otherwise indicated, any % value is based on the relative weight of the component or components in question.

EXAMPLES

The following are Examples that illustrate the present invention. However, these Examples are in no way intended to limit the scope of the invention.

Example 1: Preparation of Sumatriptan-Containing Films

Batch formulae comprising sumatriptan as the API for each individual dose strength of sumatriptan oral films are listed in Table 1. Calculations are based on yields of 1000 doses/batch (dose size=3 cm$^2$).

TABLE 1

BATCH FORMULAE FOR PRODUCTION OF SUMATRIPTAN FILMS CONTAINING DIFFERENT DOSE STRENGTHS OF THE API.

| Component | Batch formulae for target dose strengths of sumatriptan films | | | | | | |
|---|---|---|---|---|---|---|---|
| Target dose strength | 2 mg/dose | 3 mg/dose | 5 mg/dose | 6 mg/dose | 10 mg/dose | 20 mg/dose | Function |
| Sumatriptan (g) | 2.0 | 3.2 | 5.3 | 6.4 | 11.0 | 22.0 | API |
| Sodium dihydrogen phosphate (g) | 1.34 | 1.34 | 1.34 | 1.34 | 1.34 | 1.34 | Buffering component |
| Water (mL) | 197 | 197 | 197 | 197 | 197 | 197 | Solvent |
| Sorbitol (g) | 7 | 7 | 7 | 7 | 7 | 7 | Plasticizer |
| Glycerol (g) | 7 | 7 | 7 | 7 | 7 | 7 | Plasticizer |
| Sodium alginate (g) | 26.7 | 26.7 | 26.7 | 26.7 | 26.7 | 26.7 | Film-forming polymer |
| Phosphoric acid (diluted) | q.s. to pH 5.0 | q.s. to pH 5.0 | q.s. to pH 5.0 | q.s. to pH 5.0 | q.s. to pH 5.0 | q.s. to pH 5.0 | pH adjustment |

Q.S. = QUANTUM SATIS.

The films were produced according to the following procedure:
- The majority of the purified water was added to a vessel and sodium dihydrogen phosphate monohydrate was dissolved during mixing. The sumatriptan was then added under mixing.
- The pH of the solution was adjusted to 5.0 by addition of a requisite quantity of diluted phosphoric acid. Sumatriptan was gradually dissolved during the titration and fully dissolved at pH 5.
- The batch volume was increased to the correct total amount by addition of the remainder of the purified water.
- The glycerol and sorbitol liquid, partially dehydrated, were added under mixing.
- The sodium alginate was added under mixing (in a food processor) for about 30 minutes or until a lump free dispersion was achieved, resulting in a viscous cast.
- The cast was poured onto a glass plate and spreading out to a thickness of 1 mm by means of an applicator.
- The cast layer was dried in a drying cabinet heated to approximately 55-60° C. until a residual water content of from 9 to 11% by weight was achieved and a solid film was formed.
- The solid film was cut into pieces measuring 15×20 mm with a knife.
- The resulting films were placed individually into aluminium pouches, sealed with a heat sealer and labelled.

After manufacture, each batch was evaluated with respect to the following criteria:

| Property | Control |
|---|---|
| 1. Cast texture: | lump free, homogenous viscous cast (visual inspection) free of bubble prior to coating (visual inspection) |
| 2. Residual moisture*: | 9-11% (in process control) |
| 3. Film appearance**: | translucent and colour homogenous (visual inspection) smooth and flat surface structure (visual inspection) pliable and flexible (visual inspection) |

-continued

| Property | Control |
|---|---|
| 4. Dose weight homogeneity: | weighing of doses within film batches |
| 5. Sumatriptan content***: | target dose strength within ±10% (RPC-HPLC analysis) |

*Residual moisture: IR-induced water vaporization combined with real-time weight measurement was used. Percent of change in weight at start until no further change was observed as the measure of residual moisture.
**Some film batches were inspected and analysed with respect to surface structure and film homogeneity with electron microscopy and differential scanning colorimetry.
***Sumatriptan content and homogeneity: HPLC-RPC separation with detection at 220 and 282 nm was used. Amount sumatriptan/dose was calculated using a sumatriptan standard curve.

Below is an assessment of the film batches with reference to the set criteria.

1. Cast Texture

Lump free, homogenous (yellowish) viscous casts could be prepared with each individual batch formula/protocol. (Viscosity increases with sumatriptan content.)

Sumatriptan was fully dissolved in the liquid phase when pH was adjusted to 5. Since sumatriptan in itself has buffering capacity, the amount of phosphoric acid needed for pH adjustment was adjusted to each individual batch formula/protocol so as not to exceed the set batch volume.

Air bubbles, which were generated during preparation of the casts and which give inhomogeneous films containing air bubbles, were removed by leaving the cast overnight (over 15 hours) at room temperature for passive de-aeration prior to coating.

3. Film Appearance

All films prepared were translucent, smooth, had flat surface structures and flexible properties when dried to a water content of 9-11%. The 2 mg films were colourless to slightly yellow. The colour intensity of the films increases slightly with increased sumatriptan content, but were all films remained translucent and homogenous.

The films had a smooth and flat surface. They were all pliable, flexible and easy to handle.

Electron micrographs of films show that the produced films are homogenous. The 20 mg films are homogenous, but do contain small spots, which most likely are small crystals of sumatriptan. Thermal analysis of a 20 mg sumatriptan film with differential scanning calorimetry (DSC) suggests the presence of sumatriptan in crystal form in the 20 mg film as indicated by a slight peak at 170° C. (see FIG. 1).

4. Dose Weight Homogeneity

Preliminary dose homogeneity assessments suggested that unacceptably high variation was observed in films coated in one step with a ZUA applicator (Zehntner GmbH, Switzerland). This was thought to be caused by a non-continuous supply of cast/mass during the coating step. A lower dose weight variation was achieved by using a two-step coating procedure:

Step 1: coating using a 2.0 mm slit height on the ZUA applicator

Step 2: distribution of the 2.0 mm cast layer by coating with a 1.0 mm slit height on the ZUA applicator.

This process appears to result in an evenly distributed layer of cast/mass and may be a prerequisite for a more continuous supply of cast/mass during the second coating step. Homogeneity data (i.e. mg sumatriptan/mg film) for films produced using the two-step procedure show very good consistency both within batches but also between batches for each individual dose strength.

5. Sumatriptan Content

Figure 2:
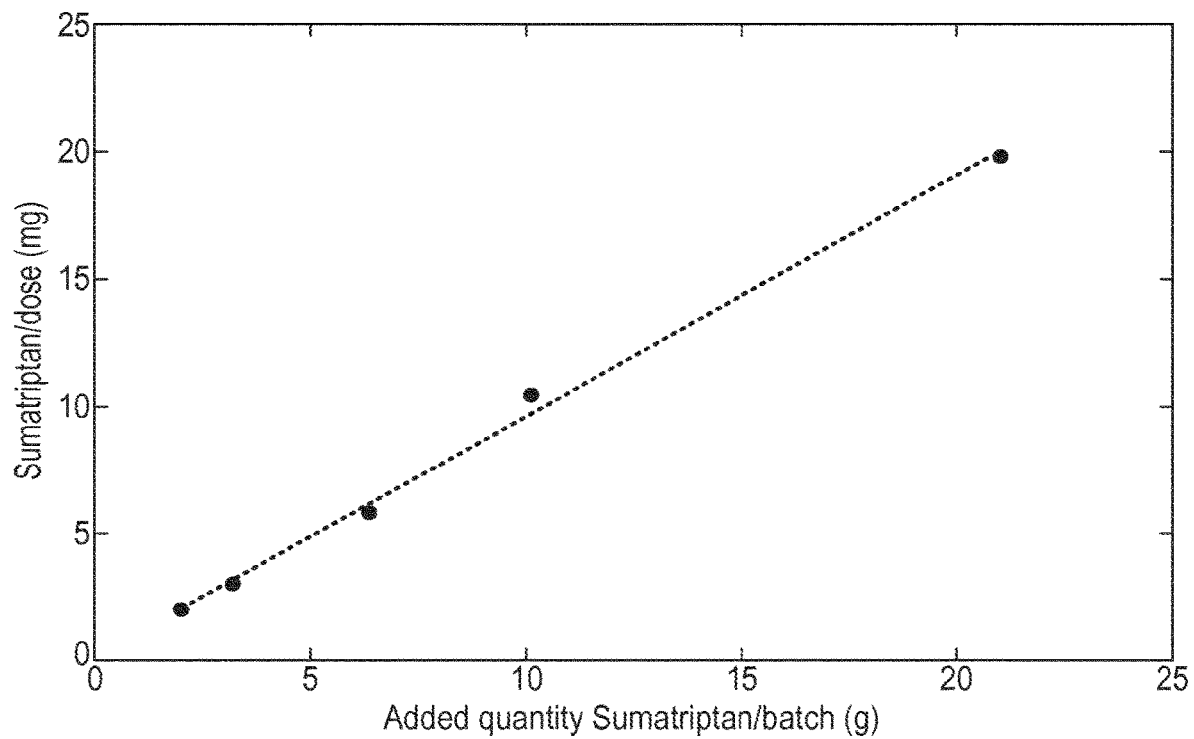
FIG. 2: Correlation between the added quantity of sumatriptan/batch and the achieved amount of sumatriptan/dose. The observed correlation is linear.

A linear correlation was found between the added quantity of sumatriptan/batch and the achieved amount of sumatriptan/dose. This is illustrated in FIG. 2. The results are based on results from initial batches from each individual batch formula/protocol.

The quantity of sumatriptan needed for each individual dose strength (2, 3, 5, 6, 10 and 20 mg) were adjusted until films with target dose strengths were obtained. Three batches of each individual batch formula/protocol were made on separate occasions to verify the reproducibility. Results from reproducibility studies for each dose strength are given in the tables below. (RSD %=relative standard deviation, expressed as a percentage.)

TABLE 2

Weight, dose and homogeneity data from three batches of 2 mg sumatriptan films.

| | Weight (mg) | Dose (mg/dose) | Homogeneity (mg sumatriptan/mg film) |
|---|---|---|---|
| Sumatriptan 2 mg Tech batch #10 (2.0 g sumatriptan in batch) | | | |
| Average | 38.4 | 2.0 | 0.053 |
| Standard deviation | 0.4 | 0.1 | 0.003 |
| RSD % | 1.0 | 5 | 5.6 |
| Number of samples analyzed | | 6 | |
| Sumatriptan 2 mg Tech batch #11 (2.0 g sumatriptan in batch) | | | |
| Average | 38.8 | 1.9 | 0.050 |
| Standard deviation | 0.8 | 0.03 | 0.002 |
| RSD % | 2.1 | 1.6 | 4 |
| Number of samples analyzed | | 8 | |

TABLE 2-continued

Weight, dose and homogeneity data from three batches of 2 mg sumatriptan films.

| | Weight (mg) | Dose (mg/dose) | Homogeneity (mg sumatriptan/mg film) |
|---|---|---|---|
| Sumatriptan 2 mg Tech batch #12 (2.0 g sumatriptan in batch) | | | |
| Average | 38.0 | 2.0 | 0.052 |
| Standard deviation | 0.7 | 0.03 | 0.001 |
| RSD % | 1.8 | 1.5 | 1.9 |
| Number of samples analyzed | | 8 | |

TABLE 3

Summary of results for three batches of 2 mg sumatriptan films. Variation within sumatriptan 2 mg batches #10-12

| | Weight (mg) | Dose (mg/dose) | Homogeneity (mg sumatriptan/mg film) |
|---|---|---|---|
| Average | 38.4 | 2.0 | 0.051 |
| Standard deviation | 0.8 | 0.07 | 0.002 |
| RSD % | 2.1 | 3.5 | 3.9 |
| Number of samples analyzed | | 22 | |

TABLE 4

Weight, dose and homogeneity data from three batches of 3 mg sumatriptan films.

| | Weight (mg) | Dose (mg/dose) | Homogeneity (mg sumatriptan/mg film) |
|---|---|---|---|
| Sumatriptan 3 mg Tech batch #2 (3.2 g sumatriptan in batch) | | | |
| Average | 43.4 | 3.1 | 0.072 |
| Standard deviation | 2.2 | 0.1 | 0.001 |
| RSD % | 5.1 | 3.2 | 1.4 |
| Number of samples analyzed | | 8 | |
| Sumatriptan 3 mg Tech batch #3 (3.1 g sumatriptan in batch) | | | |
| Average | 39.7 | 2.8 | 0.071 |
| Standard deviation | 0.5 | 0.1 | 0.001 |
| RSD % | 1.3 | 3.6 | 1.4 |
| Number of samples analyzed | | 8 | |
| Sumatriptan 3 mg Tech batch #4 (3.3 g sumatriptan in batch) | | | |
| Average | 41.1 | 3.0 | 0.072 |
| Standard deviation | 1.6 | 0.1 | 0.001 |
| RSD % | 3.9 | 3.3 | 1.4 |
| Number of samples analyzed | | 8 | |

TABLE 5

Summary of results for three batches of 3 mg sumatriptan films. Variation within sumatriptan 3 mg batches #2-4

| | Weight (mg) | Dose (mg/dose) | Homogeneity (mg sumatriptan/mg film) |
|---|---|---|---|
| Average | 41.4 | 3.0 | 0.072 |
| Standard deviation | 2.1 | 0.15 | 0.001 |
| RSD % | 5.1 | 5.0 | 1.4 |
| Number of samples analyzed | | 24 | |

TABLE 6

Weight, dose and homogeneity data from three batches of 5 mg sumatriptan films.

| | Weight (mg) | Dose (mg/dose) | Homogeneity (mg sumatriptan/mg film) |
|---|---|---|---|
| Sumatriptan 5 mg Tech batch #2 (5.3 g sumatriptan in batch) | | | |
| Average | 43.6 | 4.9 | 0.113 |
| Standard deviation | 1.9 | 0.2 | 0.007 |
| RSD % | 4.4 | 4.1 | 6.2 |
| Number of samples analyzed | | 8 | |
| Sumatriptan 5 mg Tech batch #3 (5.3 g sumatriptan in batch) | | | |
| Average | 46.2 | 5.0 | 0.107 |
| Standard deviation | 1.3 | 0.2 | 0.001 |
| RSD % | 2.8 | 4.0 | 0.9 |
| Number of samples analyzed | | 8 | |
| Sumatriptan 5 mg Tech batch #5 (5.3 g Sumatriptan in batch) | | | |
| Average | 45.6 | 5.4 | 0.119 |
| Standard deviation | 1.8 | 0.2 | 0.001 |
| RSD % | 3.9 | 3.7 | 0.8 |
| Number of samples analyzed | | 8 | |

TABLE 7

Summary of results for three batches of 5 mg sumatriptan films. Variation within sumatriptan 5 mg batches #2, 3 and 5

| | Weight (mg) | Dose (mg/dose) | Homogeneity (mg sumatriptan/mg film) |
|---|---|---|---|
| Average | 45.1 | 5.1 | 0.113 |
| Standard deviation | 2.0 | 0.3 | 0.006 |
| RSD % | 4.4 | 5.9 | 5.3 |
| Number of samples analyzed | | 24 | |

TABLE 8

Weight, dose and homogeneity data from two batches of 6 mg sumatriptan films.

| | Weight (mg) | Dose (mg/dose) | Homogeneity (mg sumatriptan/mg film) |
|---|---|---|---|
| Sumatriptan 6 mg Tech batch #1 (6.4 g sumatriptan in batch) | | | |
| Average | 43.6 | 4.9 | 0.113 |
| Standard deviation | 1.9 | 0.2 | 0.007 |
| RSD % | 4.3 | 4.1 | 6.2 |
| Number of samples analyzed | | 8 | |
| Sumatriptan 6 mg Tech batch #2 (6.4 g sumatriptan in batch) | | | |
| Average | 46.2 | 5.0 | 0.107 |
| Standard deviation | 1.3 | 0.2 | 0.001 |
| RSD % | 2.8 | 4.0 | 0.9 |
| Number of samples analyzed | | 8 | |

TABLE 9

Summary of results for two batches of 6 mg sumatriptan films. Variation within sumatriptan 6 mg batches #1 and 2

| | Weight (mg) | Dose (mg/dose) | Homogeneity (mg sumatriptan/mg film) |
|---|---|---|---|
| Average | 42.6 | 5.8 | 0.137 |
| Standard deviation | 1.7 | 0.3 | 0.004 |
| RSD % | 3.9 | 5.2 | 2.9 |
| Number of samples analyzed | | 16 | |

TABLE 10

Weight, dose and homogeneity data from three batches of 10 mg sumatriptan films.

| | Weight (mg) | Dose (mg/dose) | Homogeneity (mg sumatriptan/mg film) |
|---|---|---|---|
| Sumatriptan 10 mg Tech batch #7 (10.5 sumatriptan in batch) | | | |
| Average | 47.5 | 9.4 | 0.199 |
| Standard deviation | 0.9 | 0.15 | 0.002 |
| RSD % | 1.9 | 1.6 | 1.0 |
| Number of samples analyzed | | 8 | |
| Sumatriptan 10 mg Tech batch #8 (11 g sumatriptan in batch) | | | |
| Average | 49.0 | 10.2 | 0.208 |
| Standard deviation | 2.2 | 0.4 | 0.002 |
| RSD % | 4.4 | 3.9 | 1.0 |
| Number of samples analyzed | | 9 | |
| Sumatriptan 10 mg Tech batch #9 (11 g sumatriptan in batch) | | | |
| Average | 49.0 | 9.8 | 0.199 |
| Standard deviation | 0.8 | 0.2 | 0.001 |
| RSD % | 1.6 | 2.0 | 0.5 |
| Number of samples analyzed | | 10 | |

TABLE 11

Summary of results for three batches of 10 mg sumatriptan films. Variation within sumatriptan 10 mg batches #7-9

| | Weight (mg) | Dose (mg/dose) | Homogeneity (mg sumatriptan/mg film) |
|---|---|---|---|
| Average | 48.6 | 9.8 | 0.202 |
| Standard deviation | 1.5 | 0.4 | 0.005 |
| RSD % | 3.0 | 4.1 | 2.5 |
| Number of samples analyzed | | 27 | |

TABLE 12

Weight, dose and homogeneity data from three batches of 20 mg sumatriptan films.

| | Weight (mg) | Dose (mg/dose) | Homogeneity (mg sumatriptan/mg film) |
|---|---|---|---|
| Sumatriptan 20 mg Tech batch #5 (21 g sumatriptan in batch) | | | |
| Average | 63.4 | 18.5 | 0.291 |
| Standard deviation | 0.8 | 0.16 | 0.002 |
| RSD % | 1.3 | 0.9 | 0.7 |
| Number of samples analyzed | | 8 | |

TABLE 12-continued

Weight, dose and homogeneity data from three batches of 20 mg sumatriptan films.

| | Weight (mg) | Dose (mg/dose) | Homogeneity (mg sumatriptan/mg film) |
|---|---|---|---|
| Sumatriptan 20 mg Tech batch #6 (21 g sumatriptan in batch) | | | |
| Average | 64.3 | 19.8 | 0.309 |
| Standard deviation | 1.6 | 0.5 | 0.002 |
| RSD % | 2.5 | 2.5 | 0.6 |
| Number of samples analyzed | | 10 | |
| Sumatriptan 20 mg Tech batch #7 (22 g sumatriptan in batch) | | | |
| Average | 64.2 | 19.6 | 0.305 |
| Standard deviation | 1.3 | 1.2 | 0.016 |
| RSD % | 2.0 | 6.1 | 5.2 |
| Number of samples analyzed | | 10 | |

TABLE 13

Summary of results for three batches of 20 mg sumatriptan films. Variation within sumatriptan 20 mg batches #5-7

| | Weight (mg) | Dose (mg/dose) | Homogeneity (mg sumatriptan/mg film) |
|---|---|---|---|
| Average | 64.0 | 19.2 | 0.301 |
| Standard deviation | 1.3 | 0.95 | 0.012 |
| RSD % | 2.0 | 4.9 | 4.0 |
| Number of samples analyzed | | 28 | |

Example 2: Comparison of Sumatriptan Alginate Films with Sumatriptan Nasal Spray in Human Subjects Administration of the market-leading sumatriptan nasal spray (Imigran, 20 mg, GlaxoSmithKline) or sumatriptan oral films according to the present invention (2×18.5 mg, which were manufactured using a similar procedure to that specified in Example 1 above) to 12 healthy volunteers in a cross-over design, followed by serial blood collections and determination of sumatriptan plasma concentration, showed sumatriptan to be present in the plasma of all subjects. The 18.5 mg films used in the study had desirable physical characteristics, and were homogenous with no signs of sumatriptan crystal formation. The total weight of each 18.5 mg sumatriptan film was 64 mg. Thus, each of these films comprised 28.9% by weight of sumatriptan as active pharmaceutical ingredient.

Figure 3:
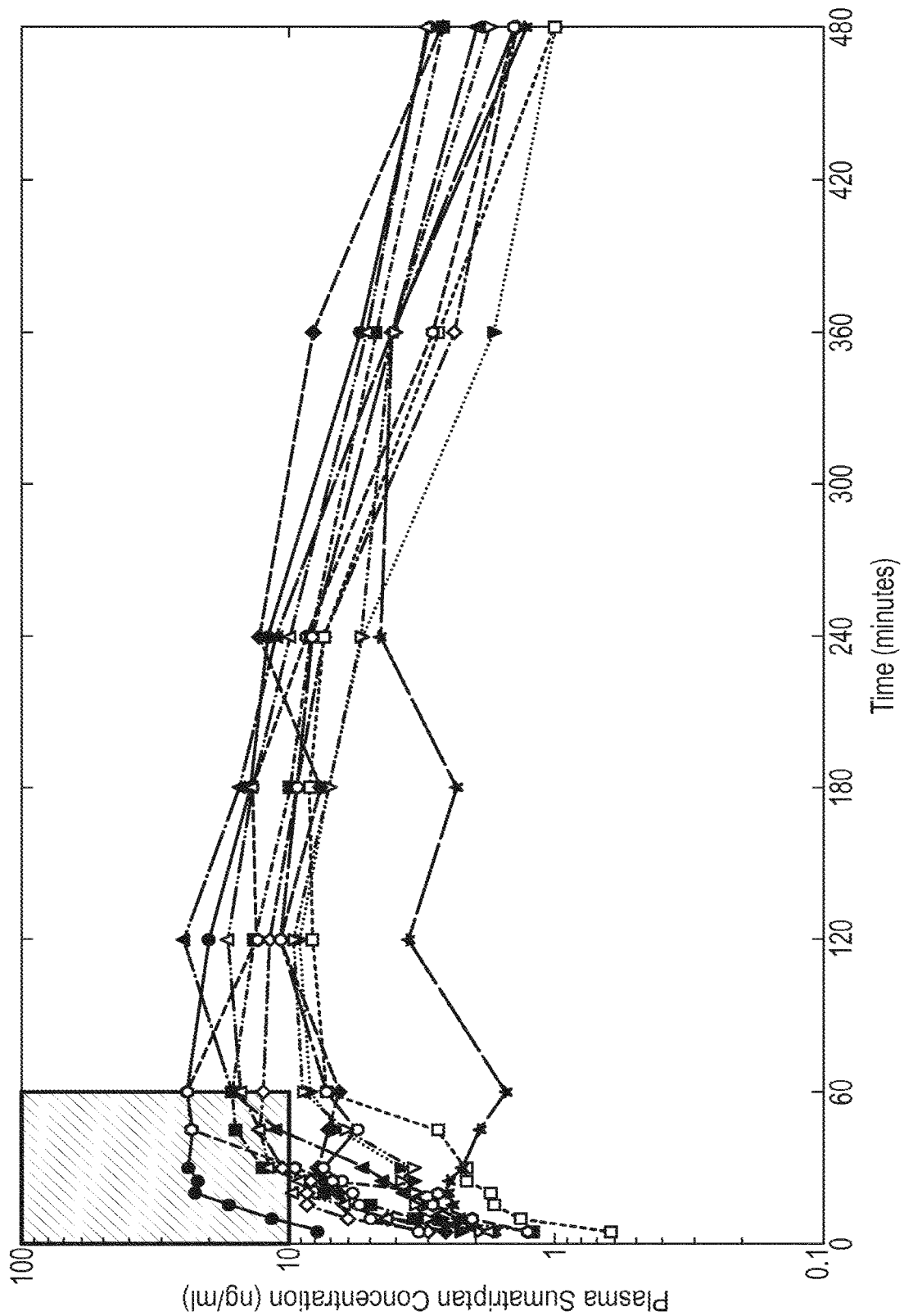
FIG. 3: Plasma concentration curves for subjects treated with a sumatriptan nasal spray. Sumatriptan plasma concentration-time curves for each of 12 persons treated with the nasal spray are displayed. Each person was treated with 20 mg sumatriptan via a nasal spray at time t=0. The grey rectangle indicates the therapeutic target window of 10 ng/mL sumatriptan in plasma within 60 minutes. 6 of the 12 subjects treated with the nasal spray reached plasma levels that are within the therapeutic target window.
Figure 4:
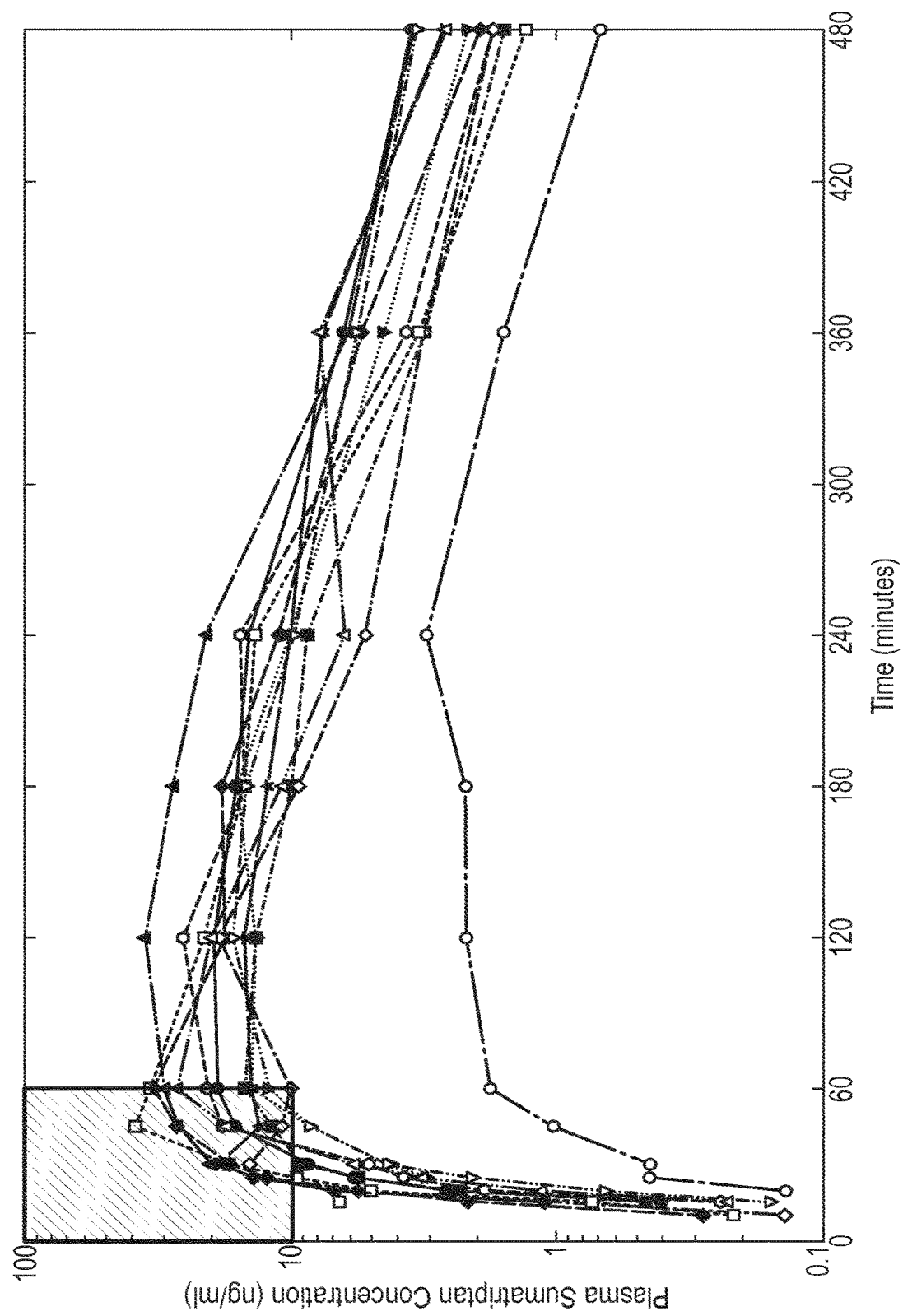
FIG. 4: Plasma concentration curves for subjects treated with a sumatriptan film administered via the oral cavity. Sumatriptan plasma concentration-time curves for each of 12 persons treated with the nasal spray are displayed. Each person was treated with 2×18.5 mg sumatriptan via an adhesive alginate film applied to the oral cavity at time t=0. The grey rectangle indicates the therapeutic target window of 10 ng/mL sumatriptan in plasma within 60 minutes. 11 of the 12 subjects treated with the film reached plasma levels that are within the therapeutic target window.

Absorption curves of sumatriptan following either nasal spray or oral film administration are shown in FIGS. 3 and 4, respectively. FIG. 3 shows individual plasma curves for the patients administering the nasal spray (20 mg); the graph also indicates the therapeutic target window of 10 ng/mL plasma within 60 minutes. The results in FIG. 3 indicate that 6 of the 12 subjects treated with the nasal spray reached plasma levels that are within the therapeutic target window. FIG. 4 shows individual plasma curves for the patients administering the OFs (2×18.5 mg); this graph too indicates the therapeutic target window of 10 ng/mL plasma within 60 minutes. The results in FIG. 4 indicate that 11 of the 12 subjects treated with the films reached plasma levels that are within the therapeutic target window.

These results therefore indicate that treatment with the films of the present invention led to significantly more patients reaching the target plasma concentration level of sumatriptan within 60 minutes than treatment with the current market-leading nasal spray. Obtaining a sumatriptan plasma concentration above 10 ng/mL plasma within 60 minutes of treatment is strongly supported to lead to the clinical end point of effective migraine relief.

Further, in the time interval between 30 and 60 minutes after administration, the coefficient of variation in the sumatriptan plasma levels of the patients treated with the sumatriptan films was c. 3-5% lower than the coefficient of variation in the sumatriptan plasma levels of the patients treated with the sumatriptan nasal spray.

Assessment of the side effects after the two treatments indicated no difference between patients treated with the nasal spray and those treated with the films.

The results also indicate that the use of alginate as film-forming agent enables the loading of a therapeutically effective amount of sumatriptan (as API) into a homogeneous film for oral use, without compromising the physical properties of the film.

REFERENCES

[1] Imigran, G. Imigran Tablets, Injection and Nasal Spray. SmPC, 2007, 24.
[2] Dechant, K L; Clissold, S P. Sumatriptan. A review of its Pharmacodynamic and Pharmacokinetic Properties, and Therapeutic Efficacy in the Acute Treatment of Migraine and Cluster Headaches. Drugs, 1992, 43(5), 776-798.
[3] Derry, C J; Derry, S; Moore, R A. Sumatriptan (all routes of administration) for acute migraine attacks in adults—overview of Cochrane reviews. The Cochrane Library, 2014, 5.
[4] https://migraine.com (accessed 11 Sep. 2016).
[5] Maas, H J; Danhof, M; Della Pasqua, O. A model-based approach to treatment comparison in acute migraine. Br J Clin Pharm 2007 62(5):591-600
[6] Ferrari, A; Pinetti, D; Bertolini, A; Coccia, C; Sternieri, E. Interindividual variability of sumatriptan pharmacokinetics and of clinical response in migraine patients. 2008 Eur J Clin Pharmacol 64:489-495.

The invention claimed is:

1. An oral transmucosal film suitable for administration to an oral cavity, comprising:
(i) an alginate salt of a monovalent cation or a mixture of alginate salts containing at least one alginate salt of a monovalent cation;
(ii) sumatriptan or a pharmaceutically acceptable salt thereof; and
(iii) citric acid, or a pharmaceutically acceptable salt of citrate, or both citric acid and a pharmaceutically acceptable salt of citrate;
wherein the alginate salt of a monovalent cation (a) comprises from 25% to 35% by weight of β-D-mannuronate and/or from 65% to 75% by weight of α-L-guluronate, and (b) has a mean molecular weight of from 30,000 g/mol to 90,000 g/mol.

2. The film according to claim 1, wherein the alginate salt of a monovalent cation is a sodium alginate, a potassium alginate or an ammonium alginate.

3. The film according to claim 2, wherein the alginate salt of a monovalent cation is a sodium alginate.

4. The film according to claim 1, wherein:
the film comprises from 25% to 99% by weight of the alginate salt of a monovalent cation or the mixture of alginate salts containing at least one alginate salt of a monovalent cation, from 0% to 20% by weight of water, and from 0.001% to 75% by weight of sumatriptan or the pharmaceutically acceptable salt thereof; or the film comprises from 30% to 86% by weight of the alginate salt of a monovalent cation or the mixture of alginate salts containing at least one alginate salt of a monovalent cation, from 5% to 15% by weight of water, and from 4% to 40% by weight of sumatriptan.

5. A method of treating migraine with or without aura, cluster headache, or trigeminal neuralgia in a human patient, wherein said method comprises administration of at least one film according to claim 1 to said human patient.

6. The method according to claim 5, wherein the film is administered to the oral cavity of the human patient.

7. A method of manufacturing a film according to claim 1, said method, comprising:
  (a) mixing sumatriptan or a pharmaceutically acceptable salt thereof and citric acid, or a pharmaceutically acceptable salt of citrate, or both citric acid and a pharmaceutically acceptable salt of citrate, in water;
  (b) adjusting the pH of the solution to the desired level by addition of an appropriate acid or base, typically a diluted aqueous acid or alkali;
  (c) optionally, adding further water and/or one or more plasticizers under further mixing;
  (d) adding the alginate salt of monovalent cation under suitable conditions to result in the formation of a viscous cast;
  (e) pouring the cast onto a surface and spreading the cast out to the desired thickness;
  (f) drying the cast layer until the residual water content of the film is from 5 to 15% by weight and a solid film is formed; and
  (g) optionally, cutting the solid film into pieces of the desired size, further optionally placing these pieces into pouches, sealing the pouches and further optionally, labelling them.

8. The method according to claim 5, wherein the human patient i) suffers from nausea and/or dysphagia and/or (ii) is additionally receiving treatment for one or more types of cancer.

9. The method according to claim 7, wherein in (b), the pH of the solution is adjusted to from 3.25 to 10.0.

10. The film according to claim 1, wherein the pharmaceutically acceptable salt of sumatriptan is succinate, tartrate, citrate, fumarate, malonate, maleate, adipate, di-mesylate, sulfate, benzenesulfonate, hydrochloride, or phosphate salts.

11. The film according to claim 1, wherein the pharmaceutically acceptable salt of citrate is a sodium salt, a potassium salt or an ammonium salt.

12. The film according to claim 1, wherein the film comprises from 0.1% to 10% by weight of the pharmaceutically acceptable salt of citrate.

13. The film according to claim 1, wherein the film comprises a buffering component which is a pharmaceutically acceptable salt of citrate and an acidifying agent which is citric acid.

14. The film according to claim 1, wherein the concentration of citric acid in the film is from 1 mM to 40 mM, or from 5 mM to 20 mM.

15. The film according to claim 1, wherein the film further comprises a plasticizer selected from polyethylene glycol, glycerol, sorbitol, xylitol or a combination thereof.

16. The film according to claim 15, wherein the film comprises from 5% to 40% by weight of glycerol and from 5% to 40% by weight of sorbitol.

17. An oral transmucosal film suitable for administration to an oral cavity, comprising:
  (i) an alginate salt of a monovalent cation or a mixture of alginate salts containing at least one alginate salt of a monovalent cation; and
  (ii) a citrate salt of sumatriptan;
  wherein the alginate salt of a monovalent cation (a) comprises from 25% to 35% by weight of β-D-mannuronate and/or from 65% to 75% by weight of α-L-guluronate, and (b) has a mean molecular weight of from 30,000 g/mol to 90,000 g/mol.

18. The film according to claim 17, wherein the alginate salt of a monovalent cation is a sodium alginate.

19. The film according to claim 17, wherein:
  the film comprises from 25% to 99% by weight of the alginate salt of a monovalent cation or the mixture of alginate salts containing at least one alginate salt of a monovalent cation, from 0% to 20% by weight of water, from 0.001% to 75% by weight of sumatriptan citrate, from 0% to 40% by weight of glycerol and from 0% to 40% by weight of sorbitol; or
  the film comprises from 30% to 86% by weight of the alginate salt of a monovalent cation or the mixture of alginate salts containing at least one alginate salt of a monovalent cation, from 5% to 15% by weight of water, from 4% to 40% by weight of sumatriptan citrate, from 5% to 40% by weight of glycerol and from 5% to 40% by weight of sorbitol.

20. A method of treating migraine with or without aura, cluster headache, or trigeminal neuralgia in a human patient, wherein said method comprises administration of at least one film according to claim 17 to a human patient,
  optionally wherein the film is administered to the oral cavity of the human patient;
  further optionally wherein the human patient (i) suffers from nausea and/or dysphagia and/or (ii) is additionally receiving treatment for one or more types of cancer.

* * * * *